United States Patent
Eggers et al.

[11] Patent Number: 5,891,142
[45] Date of Patent: Apr. 6, 1999

[54] ELECTROSURGICAL FORCEPS

[75] Inventors: Philip E. Eggers, Dublin; Andrew R. Eggers, Ostrander, both of Ohio

[73] Assignee: Eggers & Associates, Inc., Dublin, Ohio

[21] Appl. No.: 878,400

[22] Filed: Jun. 18, 1997

Related U.S. Application Data

[63] Continuation-in-part of Ser. No. 761,591, Dec. 6, 1996, abandoned.

[51] Int. Cl.$^6$ .................................................... A61B 17/39
[52] U.S. Cl. ................................................. 606/51; 606/52
[58] Field of Search ..................... 606/50–52, 43

[56] References Cited

U.S. PATENT DOCUMENTS

| | | | |
|---|---|---|---|
| 3,685,518 | 8/1972 | Beuerle et al. | 606/51 |
| 4,274,413 | 6/1981 | Hahn et al. | 606/43 |
| 4,492,231 | 1/1985 | Auth | 606/51 |

FOREIGN PATENT DOCUMENTS

| | | | |
|---|---|---|---|
| 517243 | 12/1992 | European Pat. Off. | 606/52 |

*Primary Examiner*—Lee Cohen
*Attorney, Agent, or Firm*—Mueller and Smith, LPA

[57] ABSTRACT

Surgical forceps which are configured having oppositely disposed tissue grasping surfaces at the tip regions of corresponding tines. An electrically insulative spacer assembly is positioned on and supported from at least one of the tissue grasping surfaces to space the tissue contacting surfaces apart an optimized distance, T, when the tines are in a substantially closed orientation. A preferred, strip form of spacer assembly formed of an electrically insulative material is employed and improved current paths are defined between the grasping surfaces to derive an efficient and effective hemostasis substantially without sticking of tissue to the surfaces. The geometric configuration of the spacer regions functions to enhance cleanability of the forceps and the tines of the forceps additionally are formed with side and nose surfaces at the tip regions having effective side surface current delivery areas improving forceps performance when used in a coagulative painting modality.

87 Claims, 13 Drawing Sheets

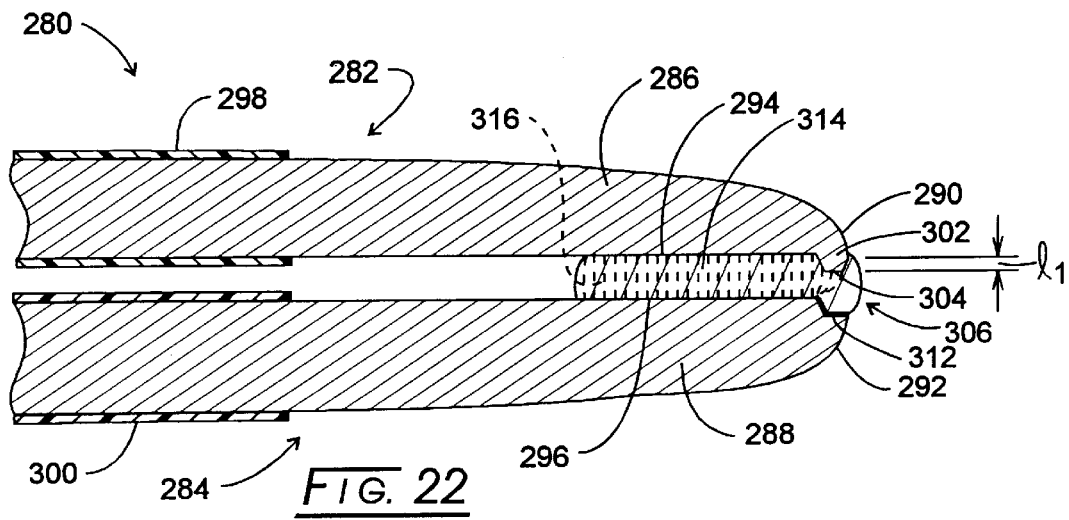
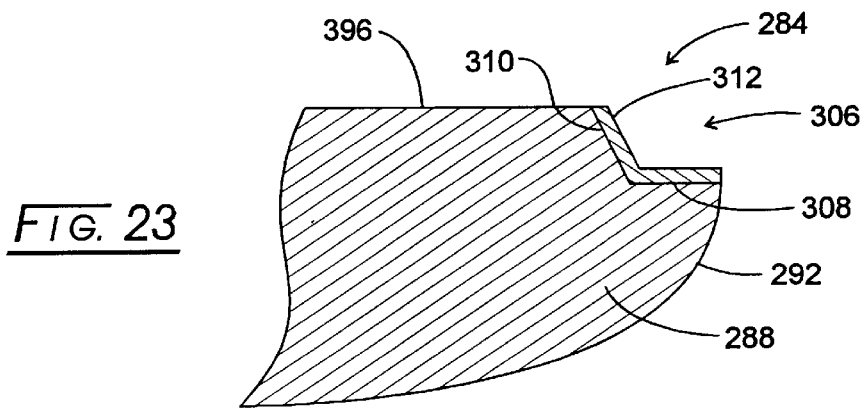
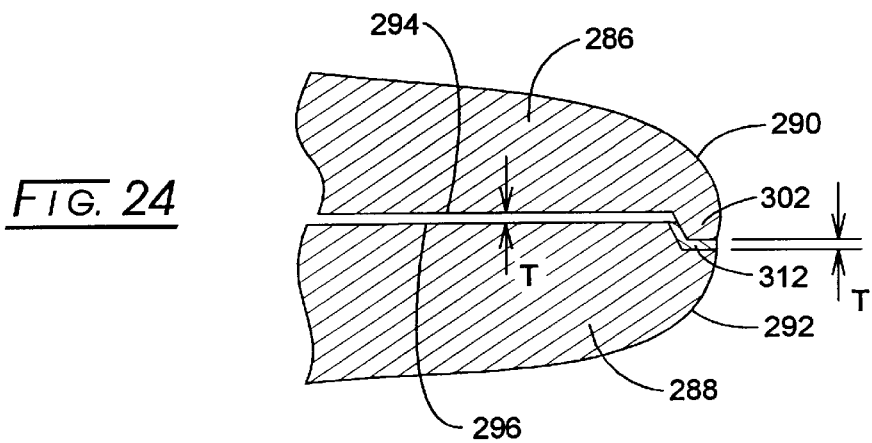

ELECTROSURGICAL FORCEPS

CROSS-REFERENCE TO RELATED APPLICATIONS

This application is a continuation-in-part of United States application for patent Ser. No. 08/761,591, filed Dec. 6, 1996, entitled "Electrosurgical Forceps", now abandoned.

STATEMENT REGARDING FEDERALLY SPONSORED RESEARCH

Not applicable.

BACKGROUND OF THE INVENTION

Surgical procedures necessarily involve the transection of vessels as surgeons seek to explore, remove, or repair tissue defined systems. Transection is carried out with a variety of cutting instruments ranging from a cold scalpel to electrosurgical devices. As such vessels are cut, it generally is necessary to accommodate bleeding by microsurgical or similar approaches, or where smaller vessels are encountered, by a sealing and congealing procedure. This latter procedure typically is carried out by heating the involved tissue and fluids through the application of electrical current at RF frequencies developed by an electrosurgical generator. Effective sealing of smaller vessels is important to surgical procedures, inasmuch as even a small blood flow not only can obscure the surgeon's field of view, but also may accumulate with the risk of hematoma or significant blood loss.

While a variety of electrosurgical instruments have been developed to achieve hemostasis, many are of marginal effectiveness for certain surgical tasks, particularly those involving small vessels and small, highly localized tissue regions of interest. To carry out such somewhat delicate surgical procedures requisite to such regions, practitioners typically employ forceps, instruments of common utility which, in effect, represent a thin extension of the thumb and forefinger function of the surgeon. Forceps generally serve to provide a tissue or vessel grasping function, having working ends or tip portions which may be of diminutive dimension enabling the surgeon to locate and grasp small vessels which have a tendency to retract into tissue following their being cut. By applying bipolar, RF current from a noted electrosurgical generator across the outer working end tips of the forceps, a sealing or congealing of tissue or vessels can be achieved without substantial risk to adjacent tissue. In effect, the well defined tips of the bipolar forceps provide a more precise attainment of hemostasis.

Another surgical application for bipolar forceps has been referred to as "coagulative painting" where typically, the side surfaces of the electrically active tip regions of the forceps' tines are drawn over the surface of membranous tissue such as the mesentery. Done properly, this action congeals the small, microvessels within such thin tissues.

Electrosurgically driven forceps heretofore made available to surgeons, however, have exhibited operational drawbacks, which, in turn, have compromised their surgical effectiveness. To effectively carry out hemostasis, the electrically operative tips of the forceps should efficiently conduct a proper current flow through the tissue grasped. When that current is insufficient, coagulation of the tissue or vessel is compromised. When the current is excessive, correspondingly excessive heating occurs with a potential for the generation of damaging electrical arcing. Excessive heating also results in the phenomenon of tissue and blood coagulum sticking to the surface of the instrument. This results in the development of a layer of increased electrical impedance between the electrodes of the instrument and that tissue which may subsequently be grasped for the purpose of treatment. Additionally, such sticking tissue evokes a disruption of the coagulated surface which, in itself, may compromise the intended hemostatic effect. Consequently, bipolar forceps designs have been seen to incorporate highly polished electrode surfaces for the purpose of reducing the extent of tissue sticking as well as to facilitate their cleaning when sticking does occur. Unfortunately, when such modification of the forceps is carried out, the original grasping function of the forceps is substantially compromised.

Another problem encountered with the use of bipolar forceps of conventional design has been associated with their use in conjunction with thin tissue. As such tissue is grasped between the opposed bipolar electrodes of the instruments, only a low tissue related impedance is witnessed by the electrosurgical generator associated with the instrument, which conventionally reacts to decrease its output toward zero as tissue impedance approaches a zero value.

Use of the bipolar forceps also becomes problematic in conjunction with the noted "coagulative painting" procedure where the side surfaces of the instrument are drawn across the surface of membranous tissue. The electrical model involved in this procedure is one wherein current is caused to flow from the side surface of one tine, thence across a thin layer of tissue to the oppositely disposed spaced apart electrically operant tine. This calls for maintenance of the spacing between the two tines to avoid short circuiting the system and for a control over what is, in effect, a moving line source of heat applied to the affected tissue. Very often, a misjudgment may lead to the tearing of tissue in the procedure. Of course, it also is necessary for the surgeon to maintain a spacing between tine electrodes of the instrument to achieve requisite performance.

Approaches to minimizing the phenomenon of tissue sticking to the operative tips of bipolar forceps have been advanced by the medical instrument industry. For example, designs have propounded the use of forceps' legs having cross-sectional areas and which exhibit conductivity sufficiently high to maintain electrically operative portions for the instruments below threshold temperatures considered to evoke tissue sticking. Similarly, the temperature of the grasping tips of the forceps has been reduced by enlarging the cross-sectional radii of the forceps sufficiently to maintain current density and resultant tissue heating below the threshold temperature evoking sticking. See in this regard, U.S. Pat. Nos. 3,685,518; 4,492,231; and 5,196,009. However, the election of a large cross-sectional area at the grasping tips of the forceps for purposes of heat conduction compromises the basically sought precision of the forceps type instrument with respect to grasping and localized coagulation of smaller blood vessels, e.g. vessels smaller than about 1 mm in diameter.

An approach to limiting the heating of the tissue or vessel being coagulated with bipolar forceps has been to utilize a layer of a ceramic material having a thermal conductivity much lower than that of the metal used in the structure of the forceps. U.S. Pat. No. 5,151,102 describes such an arrangement wherein a plurality of silver filled epoxy electrodes are embedded within the ceramic coatings. However, Joulean heating with bipolar systems occurs within the tissue which, for such arrangements, has no effective pathway through which to dissipate, resulting in an enhancement of the sticking problem which now occurs at the ceramic layer.

To regain the originally desired grasping feature of forceps, the utilization of a roughened or tooth-like surface in conjunction with the electrically operative ends of the forceps has been proposed as represented in U.S. Pat. Nos. 5,330,471 and 5,391,166. By disposing a layer of insulation on the teeth of one or both of the grasping surfaces, electrical current only passes along the sides of the electrode surfaces which are outwardly disposed from the grasping surfaces. Thus, the utility of the forceps is compromised to the extent that only thicker tissues can be grasped and coagulated efficiently. In general, serrated or multi-pyramidally configured grasping surfaces prove difficult to clean during surgery due to the recesses and grooves which tend to trap tissue debris and coagulum.

U.S. Pat. No. 5,403,312 describes a combination of an electrosurgical forceps form of instrument which additionally carries out a stapling function. Intended for the grasping of thicker tissue components, the device described employs operative forceps tips with mutually offset or staggered electrode regions suitable for more extended thickness' of tissue as opposed to thin tissue. By mounting the electrode regions within a plastic support member, an otherwise desired feature for heat removal is compromised permitting the electrodes to reach temperatures during tissue coagulation that can exceed sticking threshold temperatures with the noted undesirable cleaning requirements.

Some investigators have proposed the utilization of temperature sensors such as thermocouples which are incorporated within the bipolar forceps instruments. Propounded in U.S. Pat. Nos. 5,443,463; 4,938,761; and 5,540,684, the approach requires that a special control system be provided which precludes the utilization of the ubiquitous conventional electrosurgical generator currently available in operating theaters throughout the world. Further, the otherwise simple construction of the forceps must be abandoned to a less desirable, highly complex instrumentation with such an approach.

BRIEF SUMMARY OF THE INVENTION

The present invention is addressed to improved surgical forceps and the methods by which they may be used with the bipolar outputs of electosurgical generators of conventional design and which achieve a highly efficient hemostasis of grasped tissue or vessels. This result is realized through the development of current paths exhibiting desirable current densities and more ideal current path configurations. These forceps employ electrically insulative spacer regions or assemblies in conjunction with the mutually inwardly facing electrically conductive tissue grasping surfaces of the two movable tines of the instruments. The spacer arrangement serves to space the tissue grasping surfaces apart an optimum distance, T, when substantially in a closed orientation. Configurations for this spacer assembly achieve the ideal current path lengths developing hemostasis without the presence of recurrent sticking phenomenon. This avoidance of sticking is achieved while the grasping feature of the forceps is not compromised and an ability to clean them effectively and efficiently is achieved.

These spacer regions or assemblies of the present invention then provide for an importantly improved grasping of tissue even though the exposed metal portions of the grasping surfaces are made to have smooth surfaces in order to minimize sticking to tissue or coagulum and to facilitate their cleaning when tissue debris or coagulum does accumulate.

In a preferred embodiment for the forceps, the two tines thereof are formed having inwardly disposed and highly polished electrically conductive tissue grasping surfaces. Located upon one of these surfaces, for example, is an array of very thin electrically insulative regularly spaced discrete strips of electrically insulative material such as alumina. These strips are quite diminutive and barely tactilely discernible, and achieve the noted spacing distance, T, having a minimum value of about 0.005 inch. A variety of configurations for the spacer regions or assemblies are disclosed providing for the achievement of the noted operational improvements.

Preferably, the forceps of the invention are fabricated such that each tine incorporates a thermally conductive material such as copper in an amount sufficient to maintain the temperature at the tip region during typical use below about 60° C. to 85° C. This temperature regime for the forceps is predicated upon a conventional duty cycle of use and is achieved with practicality through the use of laminar composites of thermally conductive copper and mechanically stronger, particularly, higher modulus stainless steel. The electrically insulative spacers are fashioned, for example, of alumina, which readily is deposited upon one or both of the inwardly facing stainless steel surfaces. Biocompatibility of the entire forceps assemblage is maintained through an electro-deposited biocompatible metal coating such as chromium which coats both the stainless steel and copper laminate while not affecting the alumina spacer.

Another aspect of the invention looks to an improvement of that feature of surgical forceps employed to achieve the noted coagulative painting. In this regard, the tines are formed having a generally rectangular cross section at their tip regions. This cross section enhances the available current path deriving area of the side surfaces for purposes of coagulative painting. Additionally, the forceps may be made with relatively blunt nose components to permit a more localized but still effective coagulative painting.

Other objects of the invention will, in part, be obvious and will, in part, appear hereinafter.

The invention, accordingly, comprises the apparatus and method possessing the construction, combination of elements, arrangement of parts, and steps which are exemplified in the following detailed description.

BRIEF DESCRIPTION OF THE DRAWINGS

FIG. 22 is a partial sectional view of another embodiment of the invention with portions exaggerated to reveal structure;

FIG. 23 is a partial sectional view of one tip region of the embodiment of FIG. 22;

FIG. 24 is a partial sectional view of the embodiment of FIG. 22 showing tissue grasping surface spacing;

DETAILED DESCRIPTION OF THE INVENTION

Figure 1:
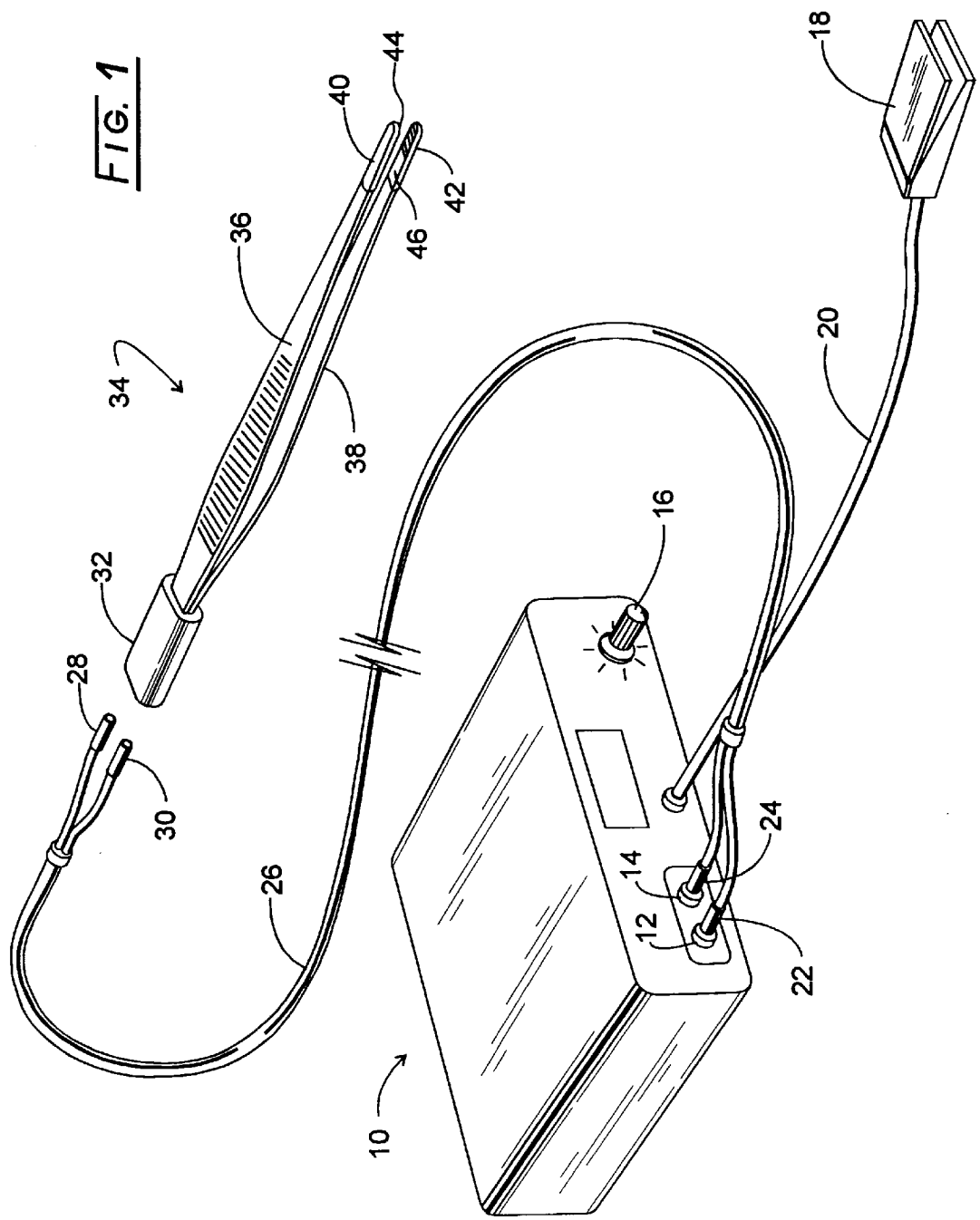
FIG. 1 is a perspective view of a bipolar forceps coupled by a bipolar cable to the bipolar terminals of an electrosurgical generator.

The bipolar electrosurgical forceps of the invention perform in conjunction with conventional electrosurgical generators having bipolar outputs. These generators are common in essentially all operating theaters and generate radio frequency voltage or power typically in response to the depression of a foot pedal on the part of the surgeon. Referring to FIG. 1, such a generator is represented generally at 10. Device 10 provides a bipolar, as opposed to monopolar, output at receptacles 12 and 14. The applied voltage level or power level at receptacles or outputs 12 and 14 may be selected by the user by adjustment of a control knob as at 16. Activation of the power outputs at receptacles 12 and 14 is provided by a foot pedal switch 18 which is connected to generator 10 via a cable 20. Outputs 12 and 14 are coupled to the respective plugs 22 and 24 of a bipolar cable 26, the opposite end of which terminates in two receptacles 28 and 30. Receptacles 28 and 30 are electrically connected with corresponding connector posts (not shown) which are recessed within a connector housing 32 of a bipolar forceps represented generally at 34. Forceps 34 are formed of two, somewhat resilient thermally and electrically conductive tines or support members 36 and 38 which are mounted within the connector housing 32 and extend longitudinally outwardly therefrom in a mutually angularly oriented fashion to respective tip regions 40 and 42. Inwardly disposed in mutual facing relationship at the tip regions 40 and 42 are electrically conductive flat tissue grasping surfaces represented, respectively, at 44 and 46. These surfaces 44 and 46 are coated with an electrically insulative material such as alumina, which, in turn, for the present embodiment is gang ground to produce a sequence of stripes or parallel bands of alternating electrically conductive metal and electrically insulative material. The stripes for surfaces 44 and 46 are mutually aligned such that when the tines 38 and 36 are squeezed to a closed or tissue grasping orientation, the electrically conductive stripes or bands at surfaces 44 and 46 move toward a mutual contact while the electrically conductive surfaces adjacent to them are mutually aligned such that a directly confronting current path through tissue may be developed between them. To provide for bipolar performance, the surfaces of tines 36 and 38 located rearwardly of the tip regions 40 and 42 are coated with an electrically insulative material such as a nylon. In general, forceps as at 34 are constructed to be sterilizable by autoclaving or the like. Tines 36 and 38 may be mounted within the connector housing 32 using an epoxy potting agent within the interior of a plastic shell. Other mounting techniques will occur to those who are art-skilled.

Figure 2:
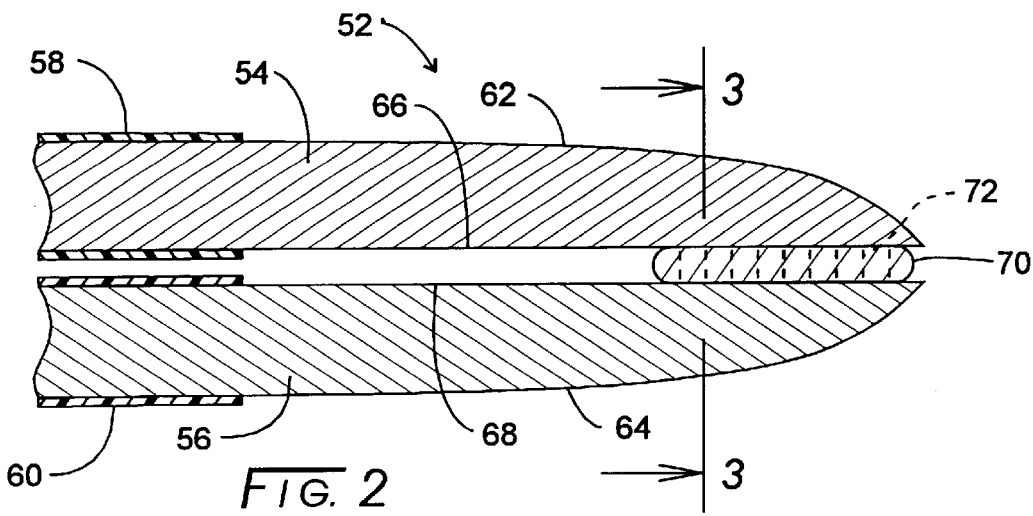
FIG. 2 is a partial sectional view of a prior art forceps.
Figure 3:
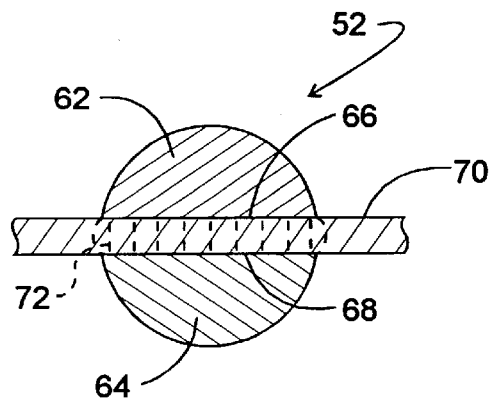
FIG. 3 is a sectional view taken through the plane 3—3 in FIG. 2.

Looking to FIGS. 2 and 3, an approach to the design of bipolar surgical forceps in the past is revealed with the purpose of analysis. In the figure, forceps 52 are fashioned having two electrically conductive tines 54 and 56, the rearwardly disposed portions of which are coated with an electrically insulative polymeric material as shown, respectively, at 58 and 60. The electrically operant tip regions of tines 54 and 56 are shown, respectively at 62 and 64. Tip regions 62 and 64 are configured having flat bare metal and polished, tissue grasping surfaces shown, respectively, at 66 and 68, and the cross-sections of the tip regions are somewhat semi-circular in configuration. Surfaces 66 and 68 are shown grasping tissue 70. Because of the smooth, all metal contact surfaces 66 and 68, upon actuation of the electrosurgical system by, for example, closing a switch such as at foot pedal 18 (FIG. 1), a radio frequency voltage difference is applied across the tip regions 62 and 64, and electrical current is caused to flow, for the most part, through the portion of tissue 70 in contact with the surfaces 66 and 68. This heats such tissue or blood vessel 70 sufficiently to carry out its thermocoagulation. While the provision of smooth grasping surfaces 66 and 68 functions advantageously to minimize the sticking of tissue or blood coagulum to such surfaces, their smoothness defeats the basic function of forceps which is to grasp tissue and hold it. Often, the tissue or blood vessel grasped at 70 slips out of the engagement before coagulation can be carried out. While the current passing through tissue 70 directly confronts it and passes therethrough to carry out Joulean heating as represented by dashed current flux lines 72, the larger contact area has been observed to promote higher current levels which, in turn, lead to higher heating rates which promotes the sticking of tissue or coagulum to the grasping surfaces 66 and 68. Often, when the tip regions 62 and 64 are opened to release the thus-coagulated tissue or vessels, sticking causes an avulsion of the sealing layer of a coagulum to somewhat defeat the procedure. In addition, even a very thin layer of desiccated tissue residue or blood coagulum will introduce a large electrical resistance at the interface between the tip regions 62 and 64 and any subsequent tissue or blood vessel which is grasped. This detracts from the operational capability of the instrument and calls for cleaning or changing instruments during the surgical procedure. Where a very thin layer of tissue is grasped or a very small vessel is grasped between the tip regions 62 and 64, a reduced load impedance is witnessed by the associated electrosurgical generator as at 10. It is the characteristic of such generators that as such load impedance reduces and approaches zero, the output voltage of the generator will decrease and approach zero volts to the extent that no voltage difference will be applied across the tip regions 62 and 64. It follows that no current for carrying out Joulean heating will flow through the grasped tissue or blood vessel and no coagulation can be achieved.

Particularly where miniature forceps are utilized, the bare tissue grasping surfaces 66 and 68 may be driven into mutual contact to cause a short circuit. This is illustrated in connection with FIG. 4 where a smaller or more diminutive tissue component 74 is seen being grasped between the grasping surfaces 66 and 68, however, those surfaces are in contact with each other in the vicinity of location 72 to cause a short circuiting. Of course, arcing is a possibility as the surfaces closely approach each other. Note that the electrically insulative coatings 58 and 60 are in contact under this geometry but often will not prevent the short circuiting.

Figure 5:
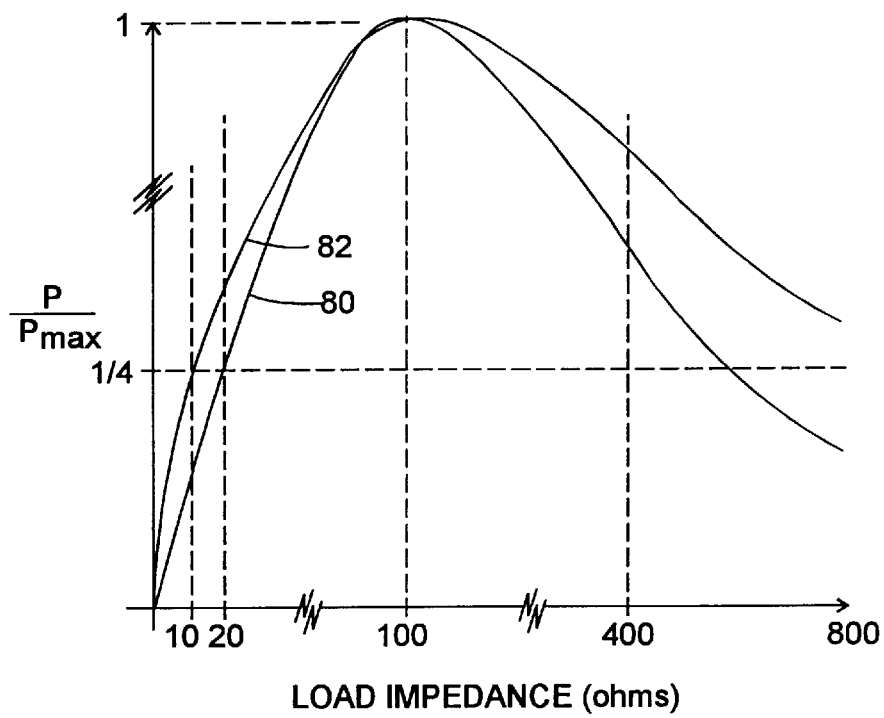
FIG. 5 is a graph relating load impedance to normalized power for two typically encountered electrosurgical generators.

To achieve a performance of bipolar forceps which approaches optimal, it is necessary to appreciate the operational characteristics of the ubiquitous electrosurgical generators which are present in essentially all operating theaters. While numerous brands of these generators are extant throughout the world, they, for the most part, have a somewhat similar output characteristic. Referring to FIG. 5, normalized curves relating load impedance to power representative of two conventionally encountered electrosurgical generators are revealed at 80 and 82. Curves 80 and 82 have similar shapes at relatively lower load impedances and, as in the case of most electrosurgical generators on the market, a maximum power output is achieved in the neighborhood of 100 ohms. As load impedance increases beyond peak value, then as evidenced by the curves, the normalized power reduces and will fall off with a characteristic somewhat associated with each individual generator. Thus, if the load impedance increases excessively, power falls off and inefficient coagulation is the result. Similarly, as the load impedance approaches zero, to the point of shorting out, no power is available also. Efficient coagulation is found to occur with load impedances somewhere in the range of 10 to 150 ohms, and the goal of the instant design is to achieve efficient coagulation for essentially most circumstances encountered in surgery with bipolar forceps while avoiding a sticking phenomena.

With the above characteristic curves in mind, it also should be observed that the electrically operant, tissue engaging grasping regions of the forceps will perform in conjunction with a load resistance which, in its simplest form, may be expressed as follows:

$$R = \frac{\rho L}{A} \qquad (1)$$

where A is the total area through which current can flow, i.e. it is the area which the current delivering surface confronts including that region which may flare out from the edge of an electrode defining portion of the forceps tissue contacting surface. L is the length of the pathway taken by the current, and $\rho$ is the characteristic resistivity of the tissue engaged.

The undesirable phenomena of sticking is not necessarily a result of the total power delivered from the forceps to the tissue but is a function of the power density or power per unit area delivered from the electrode surfaces. Thus, if the power density is controlled at the operational surfaces of the instruments, sticking may be minimized by an arrangement where current is being distributed over larger surface areas. A further aspect is concerned with the efficiency of delivering this current into the tissue to achieve a Joulean heating of it. This delivery should be the most efficient for carrying out coagulation and sealing. Coagulation should occur with the least amount of dwell time and be so localized as not to adversely affect tissue which is adjacent that being coagulated or sealed. These aspects are in the interest of both the patient and the surgeon.

Figure 6:
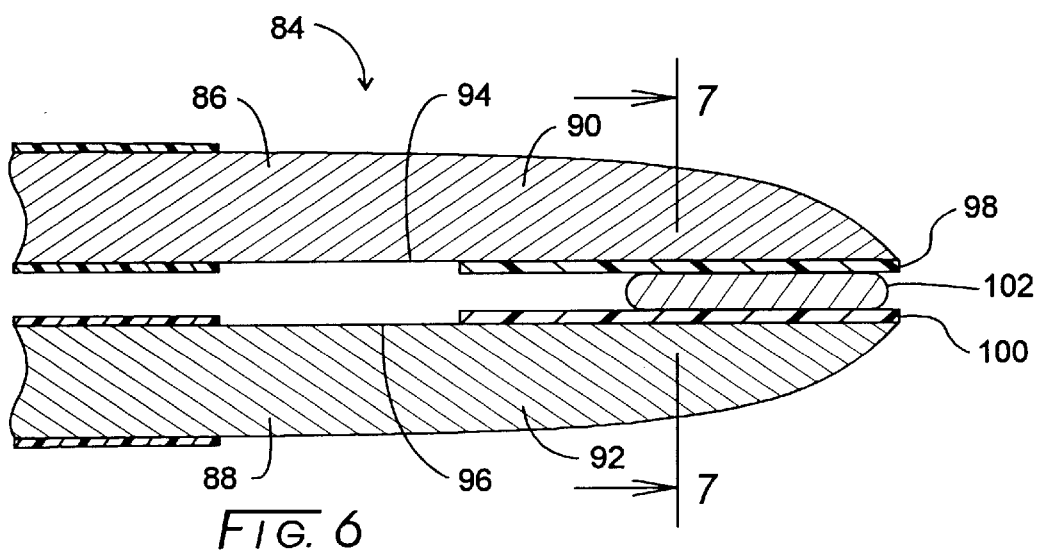
FIG. 6 is a partial sectional view of forceps of the prior art.
Figure 7:
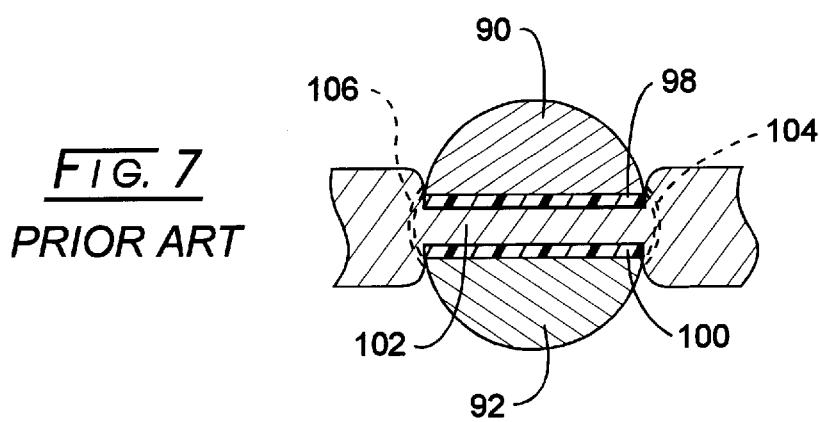
FIG. 7 is a sectional view taken through the plane 7—7 seen in FIG. 6.

Investigators have endeavored to overcome the poor grasping aspect and tendency to evoke sticking occasioned with bare surface bipolar forceps by turning to the expedient of coating the tissue grasping surfaces of the tip regions of the forceps. Looking to FIGS. 6 and 7, such an arrangement is depicted in sectional fashion. In FIG. 6, the forceps is represented in general at 84 having tines 86 and 88 with respective tip regions 90 and 92. Tip regions 90 and 92 have respective grasping surfaces 94 and 96 which, at least in part, are covered with a continuous coating of electrically insulative material shown, respectively, at 98 and 100. Continuous coatings 98 and 100 may be provided, for example, as a ceramic and thus incorporate a frictional aspect improving the tissue grasping ability of the device 84. In this regard, a component of tissue is shown in the drawings at 102. FIG. 7 reveals, however, that by so coating the grasping surfaces with a ceramic insulator, current flow is restricted essentially to the outer edges of the tip regions 90 and 92. Such a current flux path arrangement is in FIG. 7 at dashed lines 104 and 106. While the arrangement achieves improved grasping and reduced heating with a corresponding reduced likelihood of the sticking of tissue or coagulum to the grasping surfaces, if the tissue or blood vessel 102 has a small thickness, then little or no electrical contact may be achieved at the tip region edges with the result of little or no current flow. Such low current flow lowers the efficiency of requisite Joulean heating of the tissue to achieve coagulation. However, if the tissue 102 is relatively thick, then sufficient heating and coagulation may be achieved because of the added contact of electrode surface with tissue.

Figure 8:
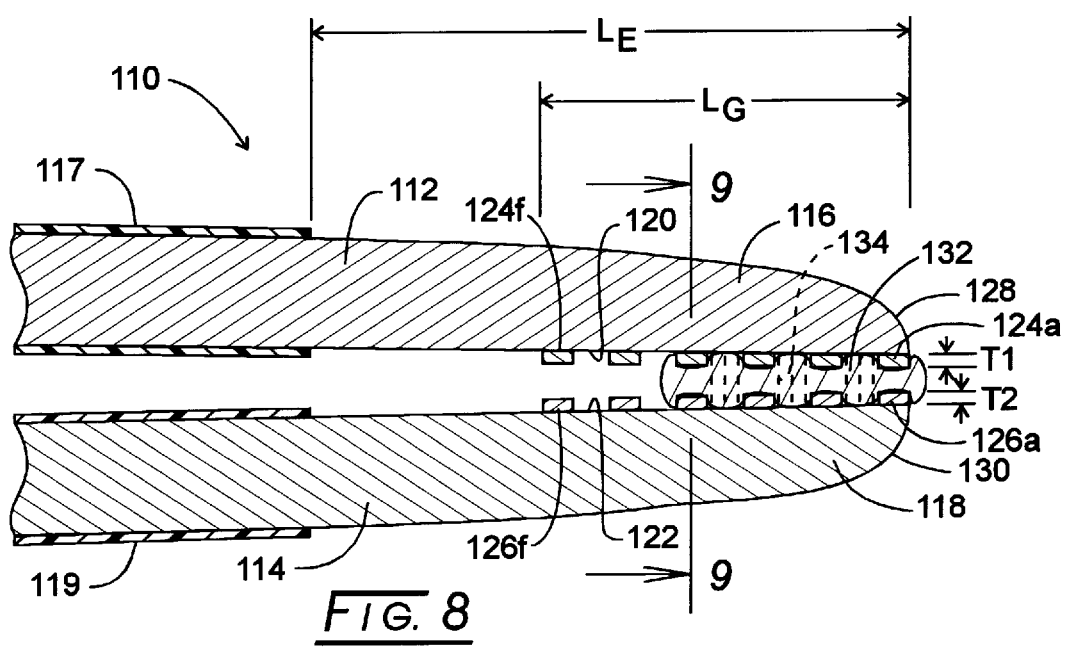
FIG. 8 is a partial sectional view of one embodiment of forceps and method of their use according to the invention with portions exaggerated to reveal structure.
Figure 9:
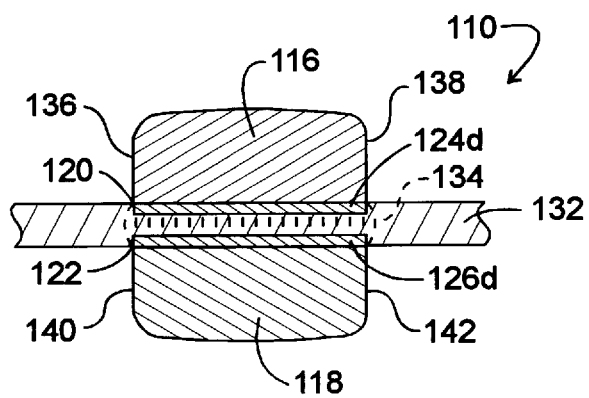
FIG. 9 is a sectional view taken through the plane 9—9 in FIG. 8.
Figure 10:
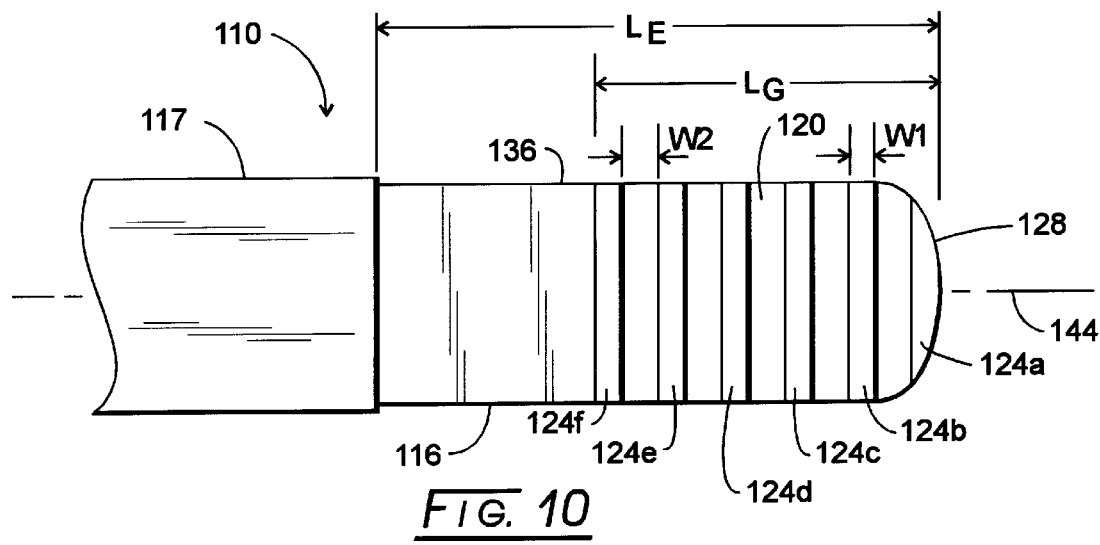
FIG. 10 is a plan view of a tip region of a tine of the forceps described in FIG. 8.

Referring to FIGS. 8–10, a depiction of an initial embodiment of forceps according to the invention is portrayed with some exaggeration of scale to facilitate the description thereof. The forceps are represented generally at 110 and include two tines 112 and 114 which are electrically conductive and extend, respectively, to tip regions 116 and 118. Rearwardly of the tip regions 116 and 118, the tines 112 and 114 are coated, respectively, with an electrically insulative coating shown, respectively, at 117 and 119. Coatings 120 and 122 preferably are formed of nylon, while the tines 112 and 114 are formed of a metal, for example, a 300 or 400 series stainless steel, nickel, tungsten, copper, or alloys of such metals. In a preferred arrangement, the tines 112 and 114 are formed of a laminar composite which combines a thermally conductive metal such as copper with a biocompatible and higher modulus metal such as stainless steel. The higher modulus of the stainless steel layer affords mechanical characteristics which more closely match conventional stainless steel forceps (e.g., forceps closure force and forceps tine deflection during grasping). In general, the stainless steel is inwardly facing to establish the base for tissue grasping surfaces. Inasmuch as certain of the thermally conductive materials such as copper are not biocompatible, the composites preferably are covered with an electrodeposited layer of a compatible material such as chromium. In addition, the inwardly facing stainless steel member (on embodiments with ceramic strips on only one side) assures that any wear of the biocompatible coating by the repeated contact with the ceramic strips will only expose an underlying layer of biocompatible metal (viz, stainless steel). Tip regions 116 and 118 are configured having inwardly disposed substantially flat tissue grasping surfaces shown, respectively, at 120 and 122. Surfaces 120 and 122 preferably are made as smooth as practical in order to avoid a sticking phenomena as much as possible. In this regard, the surfaces at 120 and 122 should meet a surface finish specification of less than 32 microinch finish or better, and preferably about 16 microinch or smoother. These highly polished surfaces become available at the grasping location of the forceps 110 because of the utilization of electrically insulative spaced apart spacer regions which are mounted, for the present embodiment, upon both of the grasping surfaces 120 and 122. The spacer regions are implemented as thin strips of alumina. In this regard, an array of such strips as at 124a–124f are provided at grasping surface 120 while a corresponding array as at 126a–126f are provided at grasping surface 120. The strips 124a–124f are shown having a thickness T1 uniformly along the array and they are evenly spaced apart longitudinally along a grasping length $L_G$. Note that this is a portion of the grasping surface 120, the entire longitudinal extent of which is represented at $L_E$. For the present embodiment, spacer regions also are mounted or formed upon grasping surface 122. In this regard, the regions are implemented as strips 126a–126f which are dimensioned and located in correspondence with the array of strips 124a–124f. The array of strips 126a–126f are shown to have a thickness T2. Note that the initial strips 124a and 126a at the respective ends or distal ends of tip regions 116 and 118 are located at the outer peripheral extents thereof. This provides an initial "snagging" geometry at the very tip of the forceps, a location most beneficial to achieving the requisite grasping function required by the surgeon. In this regard, should only one strip or region be employed with the forceps, it preferably is located at the position of strips 124a or 126a.

FIGS. 8 and 9 depict the forceps 110 as grasping a component of tissue or vessel as at 132. This is to depict one aspect of the selection of the thickness' T1 and T2 as well as the relative positioning of the strip arrays 124a–124f and 126a–126f. Note that the individual strips of these arrays both extend across the periphery of the grasping surfaces and normally to the longitudinal extent of their respective tines; they are in substantially parallel relationship, and are aligned for movement into mutual contact when in a closed orientation, at least with respect to the forward strips 124a and 126a. The thickness' T1 and T2, inter alia, are selected such that the tissue or vessel media is extruded into the recesses between the strips 124a–124f and 126a–126f to assure electrical contact with the smooth grasping surfaces as at 120 and 122 located intermediate the strips. This develops a current flux flow path as represented, for example, at dashed lines 134 which extends directly across the surfaces 120 and 122, minimizing the path length, L, and enhancing the most efficient hemostasis geometry for the instrument. It may be observed that the flux path of current in the forwardmost nose portion of the forceps 110 will flow from one exterior surface to the other in cases where the tissue has extruded outwardly about the nose surface. Importantly, such extrusion of the tissue or vessel media into the recesses between the strips serves to achieve a secure grasping thereof during its surgical manipulation and throughout the coagulation process.

FIG. 9 reveals that the cross-sections of the tip regions 116 and 118 are generally rectangular in configuration as opposed to being generally circular. In this regard, the side peripheries of tip region 116 are shown at 136 and 138, and the corresponding and aligned side peripheries of tip region 118 are shown, respectively, at 140 and 142.

FIG. 10 is a view looking into the working, grasping surface 120 of tip region 116 at tine 112. The figure reveals that the strips 124a–124f are arranged in mutually parallel relationship and extend between the peripheries 136 and 138. The figure further reveals that the array of insulated strips 124a–124f extends longitudinally along an axis 144 a grasping region length $L_G$ and that the electrically operant surface 120 extends longitudinally along a length $L_E$. The width of the individual strips is shown as W1 and the spacing of the strips defining the interstitial electrical contact surfaces is represented at W2. These spacings W1 and W2 are selected to achieve the most efficient electrode contact geometry for, in turn, achieving the most efficient hemostasis with respect to tissue or vessels grasped as described in connection with FIG. 8 above. FIG. 10 also makes evident that the utilization of parallel strips across the peripheral extent of the tip region 116 facilitates the cleaning thereof to remove any coagulation or tissue resulting from sticking. Selection of the thickness' T1 and T2 (FIG. 8) as the minimum achieving requisite grasping and efficient electrical contact also substantially facilitates cleaning procedures.

Figure 11:
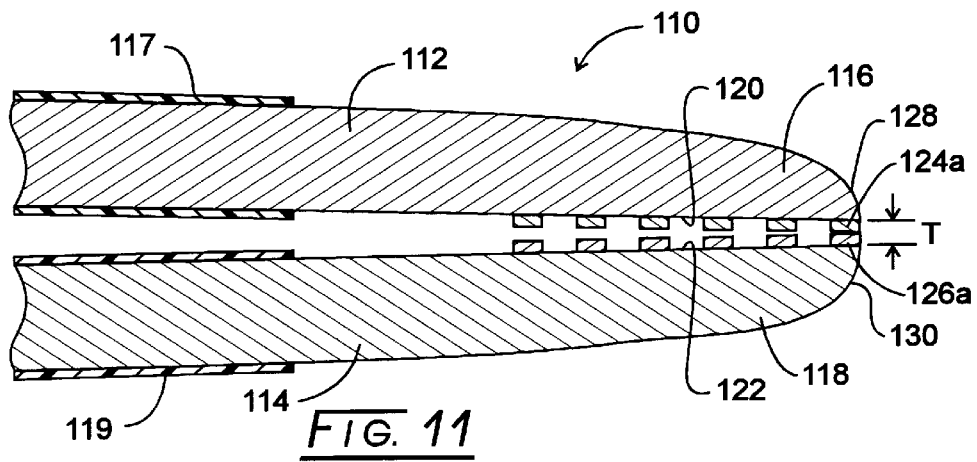
FIG. 11 is a partial sectional view of the forceps shown in FIG. 8 with a full closure orientation.

Now looking to FIG. 11, tip regions 116 and 118 of forceps 110 are reproduced with strips or insulated regions 124a and 126a having been moved into mutual contacting relationship without the presence of tissue interposed therebetween. It has been found to be beneficial to slightly bow the tines as at 112 and 114 toward each other from a location rearwardly positioned from tip regions 116 and 118. This results in an initial contact of strips 124a and 126a during a closing maneuver. Upon further pressure being made by the user, then the remaining strips progressively come into contact. Studies have shown that there are preferences in the total spacing between the grasping surfaces 120 and 122 as established by the electrically insulative region. This distance is represented in FIG. 11 as "T". This spacing, T, represents the sum of the thickness' T1 and T2 for the instant embodiment. In general, the value of the distance T, is less than 0.020 inch and is less than or equal to about 0.010 inch. The minimum value found practical for the width T is about 0.003 inch. As smaller spacings are employed, for example at values of about 0.001 inch or 0.002 inch, arcing may occur. For example, it has been found that as the value of T diminishes below about 0.005 inch, for example to 0.001 inch or 0.002 inch, when isotonic saline fluid is encountered in the surgical field and into the spacing between grasping surfaces, then an arc may form to evoke intense heating in its ionized pathway with resultant damage. In general, forceps according to the invention may have a grasping region length, $L_G$, which ranges from 0.040 to 1.2 inch (1 mm to 30 mm) and preferably 0.080 to 0.80 inch (2 mm to 20 mm). For standard size bipolar forceps, the value for the length, $L_G$, preferably is about 0.25 inch, and for microbipolar forceps, that length, $L_G$, is about 0.15 inch. Correspondingly, the overall electrically operant lengthwise extent, $L_E$, will be about 0.75 inch for standard size bipolar forceps, and 0.60 inch for microbipolar forceps. The width, W1, of the insulative strips as at 124b will, for standard size forceps, be in the range of 0.015 inch to 0.050 inch, and for microbipolar forceps in the range of from 0.010 inch to 0.040 inch. Correspondingly, the width, W2, of the bare electrode surface between adjacent strips, i.e. the interland spacing is selected in the range of about from 0.015 inch to 0.050 inch for standard size forceps and, for microbipolar forceps, in the range of from about 0.010 inch to 0.040 inch. Finally, it has been found that the thickness of the insulative coatings 117 and 119, preferably is in the range of about 0.007 inch to 0.020 inch.

The electrically insulative spacer region such as strips 124a–124f and 126a–126f may, for example, be formed of ceramic, glass, or glass/ceramic applied by plasma deposition methods; physical vapor deposition; screen or pad printing followed by fusing of the insulative layer by exposure to high temperatures; photolithography process; or attachment of individual ceramic members using brazing, soldering, or adhesive bonding methods. Of the above, the preferred method and material is the plasma deposition of alumina either by masking or followed by subsequent gang grinding.

Figure 12:
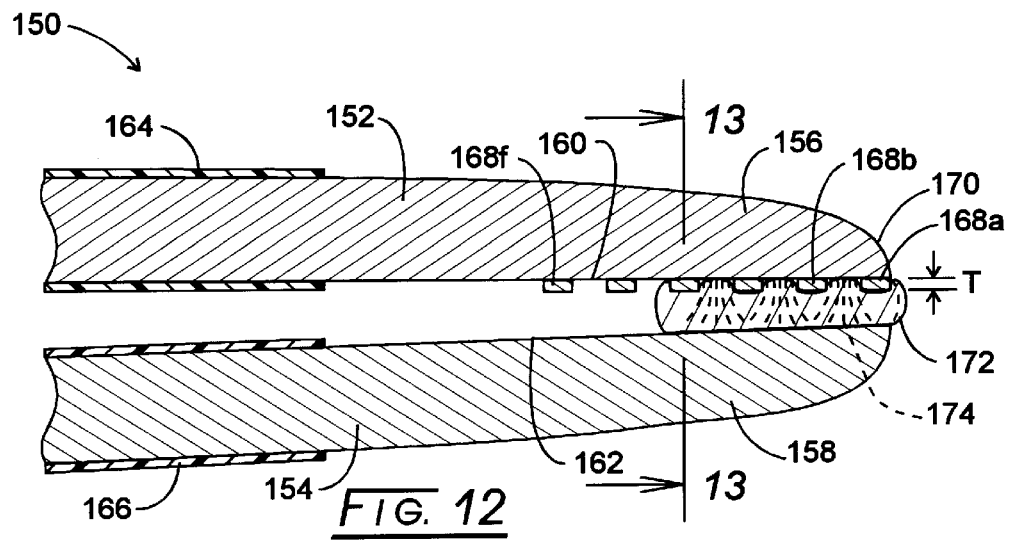
FIG. 12 is a partial sectional view of a preferred embodiment of the invention with portions exaggerated to reveal structure.
Figure 13:
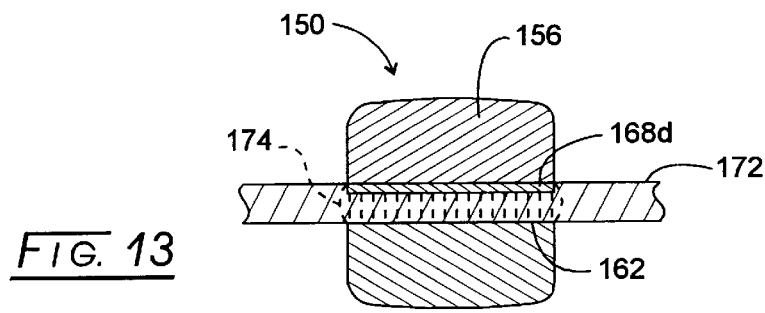
FIG. 13 is a sectional view taken through the plane 13—13 in FIG. 12.

Referring to FIGS. 12 and 13, a preferred embodiment for the tip regions of bipolar forceps according to the invention is revealed. In the figure, a forceps represented generally at 150 is shown with portions in exaggerated scale in the interest of clarity. These forceps 150 include two tines 152 and 154 which extend to respective tip regions 156 and 158. Mutually inwardly disposed at the tip regions 156 and 158, as before, are flat, electrically conductive tissue grasping surfaces shown, respectively, at 160 and 162. These surfaces should have the same smoothness characteristic as discussed above in connection with forceps 110. Tines 152 and 154 are coated with an electrically insulative coating such as nylon as represented, respectively, at 164 and 166. For the present embodiment, only one grasping surface, that at 160, is configured supporting insulative regions present as at strips 168a–168f. Surface 162 is a smooth, bare metal. In this embodiment, as before, the strip 168a is adjacent the nose profile 170 of tip region 156 to enhance the grasping function. The remaining strips 168b through 168f are parallel and regularly spaced in the manner of FIG. 10 along a grasping surface lengthwise extent, $L_G$, as discussed in connection with FIG. 10. Similarly, the widthwise dimension of the strips 168a–168f as well as their spacing is as described, respectively, at W1 and W2 in connection with FIG. 10. Experimental studies have established that this arrangement, utilizing the insulative regions at only one of the grasping surfaces, provides for the effective grasping of very thin tissue and small blood vessels. In addition, coagulation capabilities of the instrument 150 have been seen to be improved as a result of the greater electrical contact area involved. In this regard, it may be observed that a component of tissue or vessel 172 will carry current flux paths which expand through the tissue as they extend to the grasping surface 162. Current flux paths are represented by dashed lines 174 showing a broader distribution of current. As seen additionally in FIG. 13, flux paths of this embodiment also are created at the nose of the instrument 150 where tissue 172 extrudes into contact with the nose profile of forceps 150. This evokes a slight flaring out of current flux paths. An important advantage of this embodiment resides in the reduction in manufacturing costs inasmuch as the electrically insulative strip or strips need only be applied to one of the two grasping surfaces either 160 or 162. Further, manufacturing costs are reduced inasmuch as there is no requirement for precisely controlling the widths of the insulative strips 168a–168f or the spacing therebetween to assure required registration between an upper and lower disposed array of strips as in the case of the embodiment described above. This also enhances manufacturability inasmuch as a requirement for precisely registering the insulative strips at two grasping surfaces is eliminated during final assembly. It may be observed, however, that the thickness of the strips 168a–168f now is selected as the value, T, to achieve the minimum spacing between surfaces 160 and 162 deriving a current path through the grasped tissue which is of a length not exceeding the value achieving effective coagulation while avoiding arcing. Values of T have been described hereinabove.

Figure 12A:
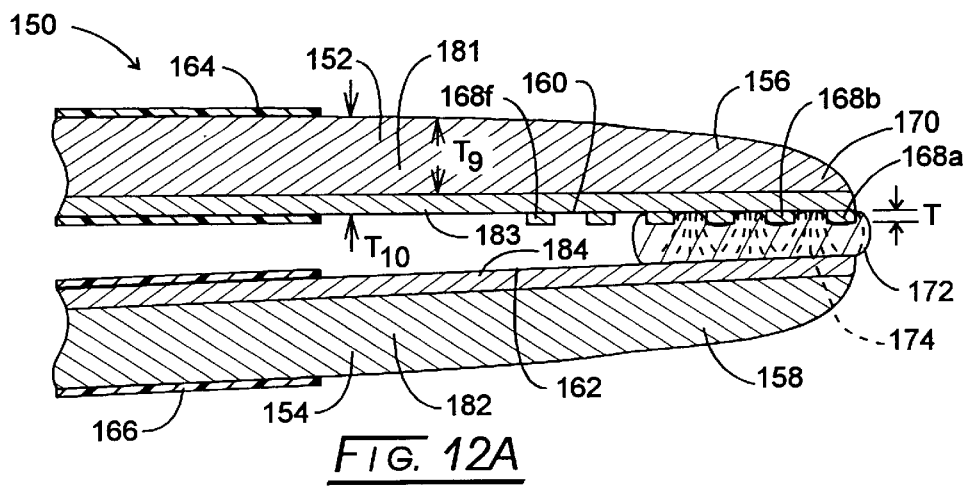
FIG. 12A is a partial sectional view according to FIG. 12 showing a laminar composite structure of tine components.

Referring additionally to FIG. 12A, constructional aspects of the preferred embodiment for forceps 150 are revealed. In the figure, each of the tines 152 and 154 is formed as a laminar composite extending the entire tine length and, importantly within the tip region shown, respectively, at 156 and 158. This composite is formed of a highly thermally conductive material such as copper as represented at 181 in the case of tine 152 and at 182 in the case of tine 154. On the internal surface of the tines there is joined to the copper both electrically and thermally a stainless steel layer as at 183 in bond with copper component 181 and as at 184 in thermal and electrical bond with copper component 182. These copper and stainless steel components may be metallurgically bonded by conventional roll bonding or roll laminating procedures. In general, the amount or mass of copper utilized is selected as being sufficient to provide a thermal conduction of heat generated during hemostasis such that the temperature of the tip regions 156 and 158 will stay below about 60° C. to 85° C. This temperature maintenance also contributes to the avoidance of sticking phenomena. The small insulative regions present as the parallel strips 168a–168f are deposited upon the stainless steel which represents a thickness of 10% to 50% of the total thickness at the tip region i.e., the composite is provided as a bonded copper and stainless steel laminate having a copper content of about 50% to 10% by volume. To complete the arrangement, the laminar composites are coated with a biocompatible metal coating which, fortuitously, may be applied after the placement of the insulative strips 168a–168f. With the arrangement, heat otherwise developed at the tip region 156 and 158 is conveyed down the tines of the instrument 150 and typically will be dissipated into the surrounding air and ultimately to the thinly gloved hand of the surgeon. Typically, the temperature rise in the proximal portion of the forceps of the present invention will not exceed about 10° C. While copper is the metal of choice for the thermally conductive components 181 and 182, other thermally conductive materials will occur to those skilled in the art, for example, silver, aluminum, tungsten, or nickel. In general, for small forceps, for example having a width of about 1 mm at their tip, the laminar composites may be provided having a layer of 304 stainless steel of thickness of about 11 mils and a corresponding layer of copper having about at 52 mils thickness. For larger forceps, the laminar composites may be provided having a layer of 304 stainless steel of thickness about 15 mils and a corresponding layer of copper having about 75 to 85 mil thickness. The biocompatible coating may be provided, for example, as an electrodeposited chromium coating, for example identified as Medcoat 2000 marketed by Electrolyzing Corporation of Ohio, Cleveland, Ohio 44112. This biocompatible coating is described as meeting or exceeding USP Class VI certification.

Figure 4:
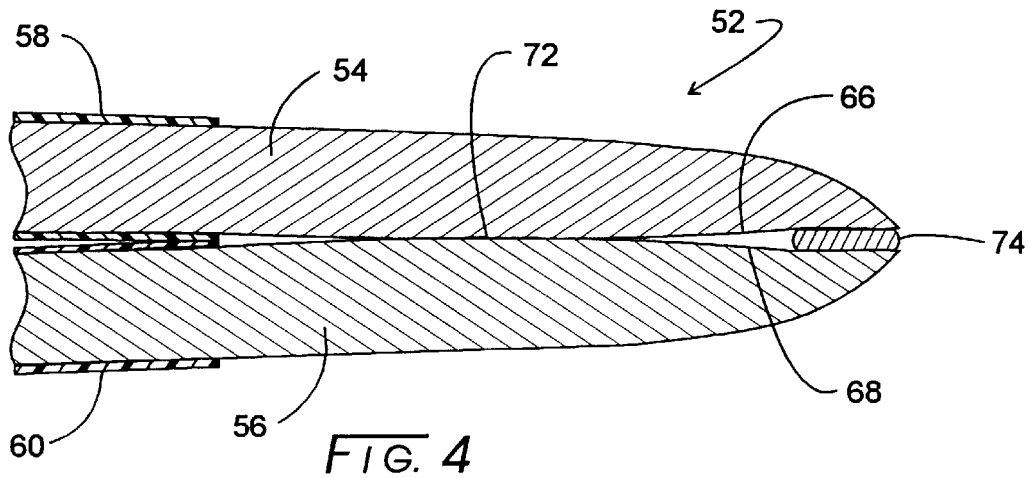
FIG. 4 is a partial sectional view of another forceps of the prior art.
Figure 14:
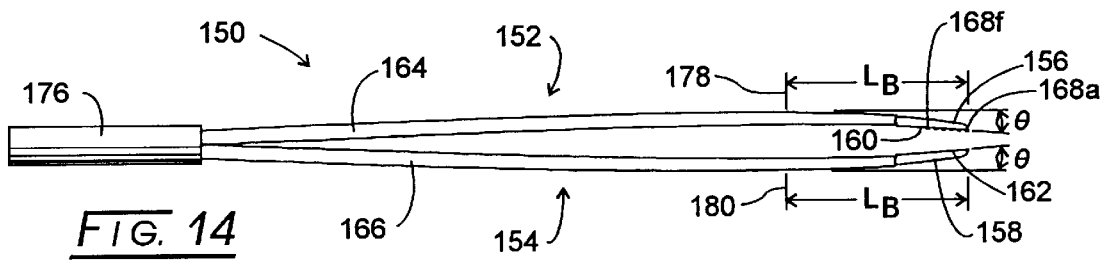
FIG. 14 is a plan view of the forceps of FIG. 12 without exaggerated dimension.

Referring to FIG. 14, a view of forceps 150 is shown without the earlier-utilized exaggerations of dimension or the like as employed for descriptive purposes. In the figure, the tines 152 and 154 are seen to extend from a connector housing 176 serving the function of that shown at 32 in connection with FIG. 1. These tines 152 and 154 are coated, respectively, with nylon coatings 164 and 166 which extend to the commencement of tip regions 156 and 158. The bare but smooth grasping surface 162 is identified as well as the corresponding surface at 160 with an associated array 168a–168f of insulative regions present as parallel strips. Because of the very small thickness of the strips 168a–168f, they are slightly, tactilely discernible but visually discernible inasmuch as there is a visual contrast between the electrically insulative coating such as alumina and the interstices of polished stainless steel. It should be noted that the surfaces of strips 168a–168f also provide a frictional aid to the engagement of tissue, including vessels, it being understood that the term "tissue" includes both anatomical components. It further may be observed that the tines 152 and 154 are both bent mutually inwardly from bend points shown, respectively, at 178 and 180. These points 178 and 180 are located a distance, $L_B$, rearwardly from the nose profiles of the tip regions 156 and 158. The bends or bowing, which preferably is identical for each side are shown to be at an angle θ with respect to the longitudinal extent of tines 152 and 154. Preferably, this angle θ will be in the range of about 1° to 10° and the bend points 178 and 180 will be at distance, $L_B$, in a range of about 1.0 to 3.0 inch for standard forceps sizes. For microbipolar forceps, the length, $L_B$, will be in the range of about 0.5 to 1.5 inch. As is apparent from the figure, as the forceps tines 152 and 154 are pushed together, the outer insulative strip 168a will eventually come into contact with the tip surface portion of grasping surface 162. Then, as further pressure is applied to the tines 152 and 154, the strips as at 168b–168f will substantially sequentially come into contact with the surface 162. The phenomena discussed in connection with FIG. 4 is avoided with this arrangement, particularly, in the case of microbipolar forceps and a desirable point grasping at the nose profile of the forceps 150 is made available to the surgeon.

Figure 15:
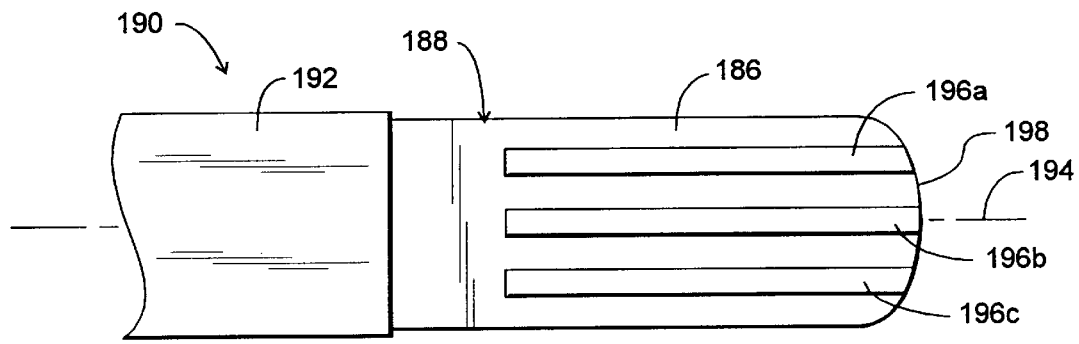
FIG. 15 is a plan view of a tip region of a tine of the forceps of another embodiment of the invention.

Looking to FIG. 15, grasping surface 186 of a tip region 188 of a tine 190 for bipolar surgical forceps is revealed. The tine 190 is coated with an electrically insulative coating 192 formed, for example, of nylon, and the tine is seen aligned along a longitudinal axis 194. For this embodiment, one or more of the electrically insulative spaced apart spacer regions are formed, for instance, as an array of parallel strips 196a–196c which are generally aligned with the axis 194 and extend outwardly to the periphery 198 of the nose portion of the tine 190. For this embodiment, a substantially electrically operant metallic surface is presented to tissue to be grasped and the frictional surface of the strips 196a–196c functions to enhance the necessary grasping function. In general, the strips 196a will have a thickness equivalent to the above-discussed value T and may be produced using a physical mask or thick film printing (e.g. glass) to deposit the electrically insulative material in the requisite areas.

Figure 16:
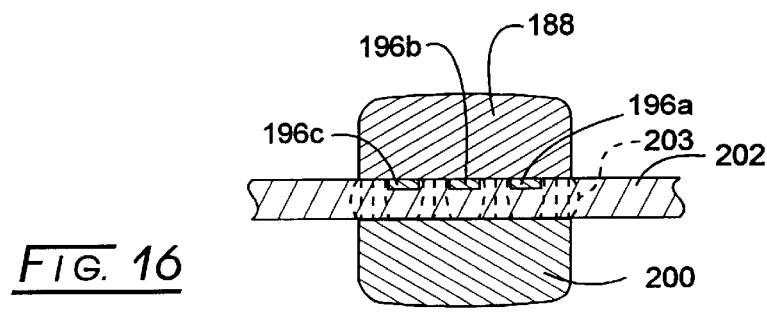
FIG. 16 is a sectional view of forceps incorporating the tip region shown in FIG. 15.
Figure 17:
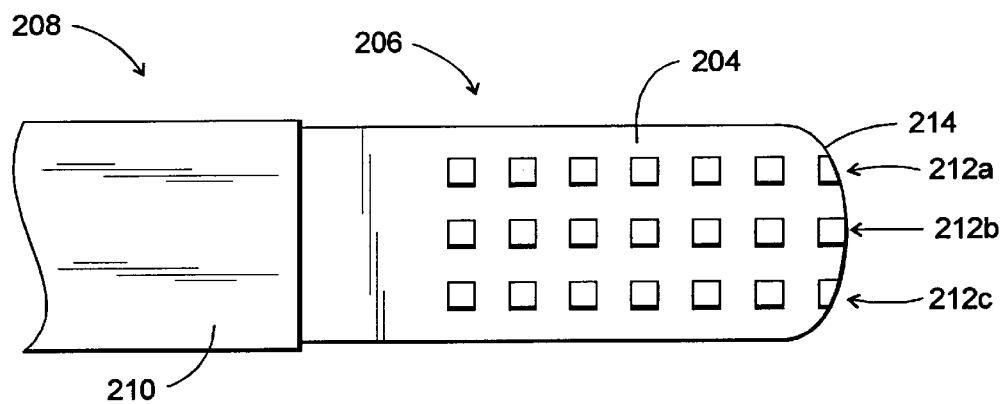
FIG. 17 is a plan view of the tip region of a tine of another embodiment of forceps according to the invention.

Looking additionally to FIG. 16, tip region 188 is seen combined with the tip region 200 of an adjacent tine (not shown) in grasping relationship with a tissue component 202. It may be observed that the configuration of FIGS. 15 and 16 enjoys a highly efficient current flux path geometry for example represented at 203, and achieves a requisite minimum spacing. The cross-sectional profile of the two tip regions 188 and 200 as observed in FIG. 16 is seen to be somewhat rectangular in shape, a shape which to promote certain coagulating procedures. Referring to FIG. 17, another embodiment of a single sided grasping surface as discussed in conjunction with FIGS. 12–15 is revealed at 204. Surface 204 is a component of tip region 206 of a tine 208 forming a portion of a bipolar forceps (not shown). The tine 208 is covered with an electrically insulative coating such as nylon as at 210. For this embodiment, the electrically insulative spacer regions are provided as discrete, spaced apart cubes disposed in three parallel linear arrays 212a–212c. The outermost of these cubes are at the nose periphery and are seen to conform with the shape thereof. Advantageously, these cube spacers are positioned to promote grasping adjacent that periphery 214. The insulative regions defined within the arrays 212a–212c may be formed by first depositing, for example by plasma deposition or physical vapor deposition, an electrically insulative layer over the desired length, $L_G$, of the grasping surface 204. Next, thin grinding wheels can be used to grind away the electrically insulative layer to produce the alternating pattern of electrically insulative rectangles. This procedure may also be employed in conjunction, for example, with the embodiments of FIGS. 8, 10, and 15. The thickness of the cubes as they protrude from surface 204 should establish the above-discussed minimum distance or spacing, T. Preferably, the insulative regions or arrays 212a–212c are formed by thick film printing of insulative material (e.g. glass) followed by exposure to elevated temperatures to effect its bonding to surface 204.

Figure 18:
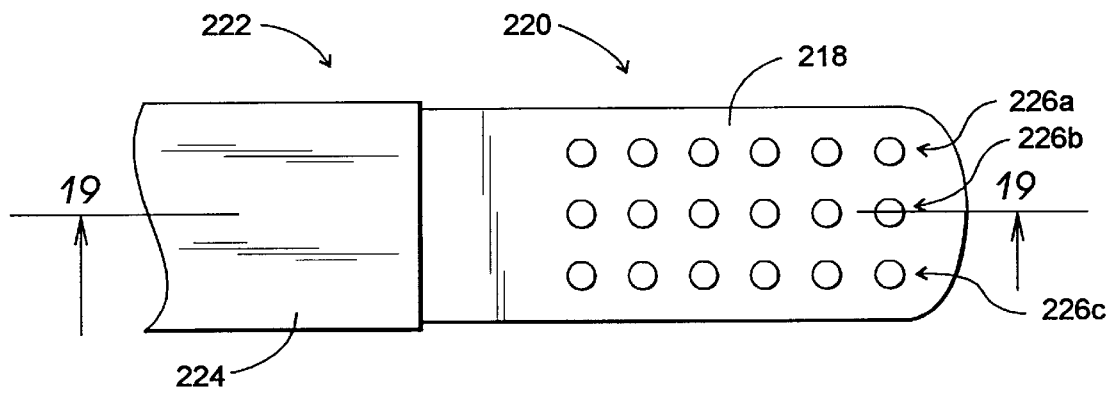
FIG. 18 is a plan view of the tip region of a tine of another embodiment of forceps according to the invention.
Figure 19:
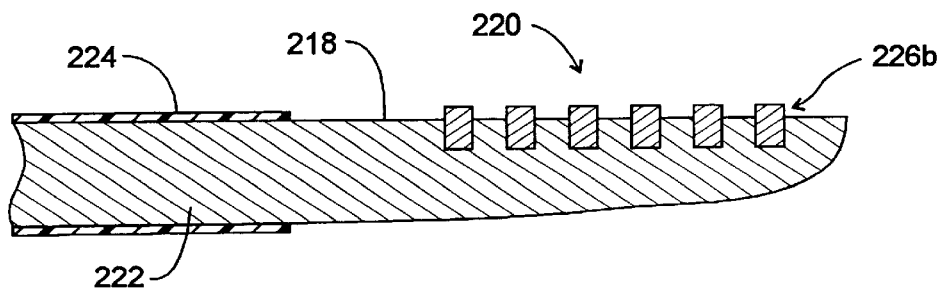
FIG. 19 is a sectional view taken through the plane 19—19 in FIG. 18.

Looking to FIG. 18, another embodiment or tip region according to the invention is revealed. In the figure, grasping surface 218 forms part of a tip region 220 which, in turn, is a component of a tine 222. Tine 222 is provided with an insulative coating 224, for example formed of nylon. For this embodiment, the electrically insulative spacer regions are provided as a regular array of discrete circular layers of thickness, T, as above described. The circular layers may be produced as regularly spaced linear arrays as an alternative to the formation of these spacers as layers, for example utilizing a physical mask to deposit the electrically insulative material in required areas. Alternatively, the tip region 220 and associated grasping surface 218 may be configured containing an array of holes of circular cross-section or peripheral shape corresponding with the linear arrays 226a–226b and 226c. The spacers forming the arrays 226a–226b then may be provided as electrically insulative glass, ceramic, or glass/ceramic pegs inserted within the holes as illustrated in the sectional view of FIG. 19.

Figure 20:
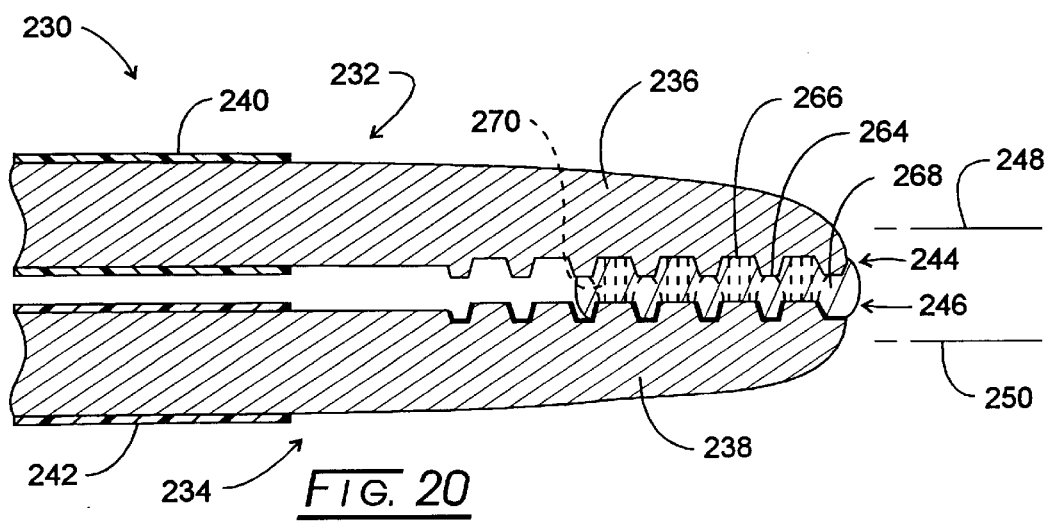
FIG. 20 is a partial sectional view of another embodiment of forceps according to the invention.

Looking to FIG. 20, another embodiment directed to enhancement of the grasping function of a forceps 230 is depicted. In the figure, the forceps 230 are shown having two tines 232 and 234 which extend to tip regions as shown, respectively, at 236 and 238. Nylon coatings as at 240 and 242 provide electrical insulation to the tines 232 and 234. Forceps 230 are designed to achieve the requisite electrode spacing, T, as well as the desirable direct path or tissue confronting type path for current flux as described hereinabove. In this regard, the tissue grasping surfaces as shown generally at 244 and 246 are grooved or corrugated with a sequence of grooves and lands which extend transversely to the longitudinal axes of tines 232 and 234 as represented, respectively, at 248 and 250. As before, only one grasping surface, that at 246, is configured with an electrically insulative coating and the extent or thickness of this coating does not necessarily determine the requisite minimum electrode surface spacing, T. Looking additionally to FIG. 21, a partial view of tip region 238 and grasping surface 246 is revealed. In this figure, the electrically insulative surface formed, for example, of alumina or the like is shown at 252 extending within a groove represented generally at 254 and having a grooved bottom surface 256. This insulating surface 252 has been ground off of the top of the next adjacent tooth-like configuration to define a land 258 of electrically conducting metal surface. These grooves and teeth are formed in successive fashion, the next insulative surface being shown in FIG. 21 at 260 as extending to a grooved bottom surface 262 in continuous fashion.

Returning to FIG. 20, the tissue grasping surface 244 of tip region 236 is similarly fashioned but with a grooved bottom corresponding to the land configuration at grasping surface 246. No electrically insulating coating is provided with respect to grasping surface 244 and the plateau or land components, one of which is identified at 264, will move into contacting adjacency with a corresponding grooved bottom arranged in registry therewith at grasping surface 246. These lands or plateaus 264 then establish the requisite spacing, T, between a land or plateau as at 258 (FIG. 21) and a corresponding grooved bottom of face 244, one of which is shown at 266. For convenience of manufacture, the electrically insulative coating at the grooved bottoms as discussed at 256 and 262 in connection with FIG. 21 will be made equivalent to the noted distance, T. FIG. 20 further reveals that the grasping surfaces 244 and 246 are engaged with a tissue or vessel component 268. Dashed lines at 270 illustrate the ideal, directly confrontational current flux paths achieved with the design.

Figure 21:
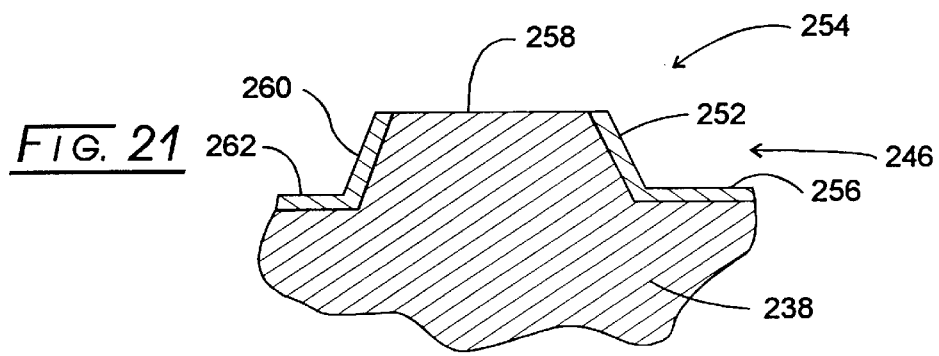
FIG. 21 is a partial sectional view of a tooth-like structure seen in FIG. 20.

The tooth-like tissue grasping surface configuration of the embodiment of FIGS. 20 and 21 also can be implemented utilizing but a single tooth forwardly disposed at the tip periphery of the tip regions. This singular tooth arrangement provides the earlier-noted "snagging" performance. Looking to FIG. 22, the singular tooth embodiment is represented by a forceps depicted generally at 280. In the figure, the forceps 280 are shown having two tines 282 and 284 which extend to tip regions as shown, respectively, at 286 and 288. These tip regions further extend to an outer periphery or tip periphery shown, respectively, at 290 and 292. The tissue grasping surfaces for the tines 282 and 284 are represented, respectively, at 294 and 296, and the rearwardly disposed portion of the forceps 280 are seen covered with an insulative coating such as nylon as represented at 298 and 300 for respective tines 282 and 284.

The tip periphery 290 is seen to be configured having an inwardly depending tooth 302 having a tooth length $l_1$ which extends to an engaging surface 304. Correspondingly, the tip periphery 292 is formed having a recess represented generally at 306. Looking additionally to FIG. 23, the recess 306 is seen to extend to a bottom surface 308 and to have a somewhat inwardly slanted side surface 310 providing a profile corresponding with that of the tooth 302. The bottom surface 308 of the recess 306 and, optionally, the slanting sidewall 310, are coated with en electrically insulative spacer layer or assembly 312. As seen in FIG. 24, the thickness of layer 312 serves to space the tissue grasping surfaces 294 and 296 apart a distance, T, in keeping with the precepts of the invention providing for optimal current flow through grasped tissue. In the latter regard, such tissue is represented in FIG. 22 at 314, while dotted lines 316 represent current paths through such tissue extending from surface 294 to surface 296.

Figure 25:
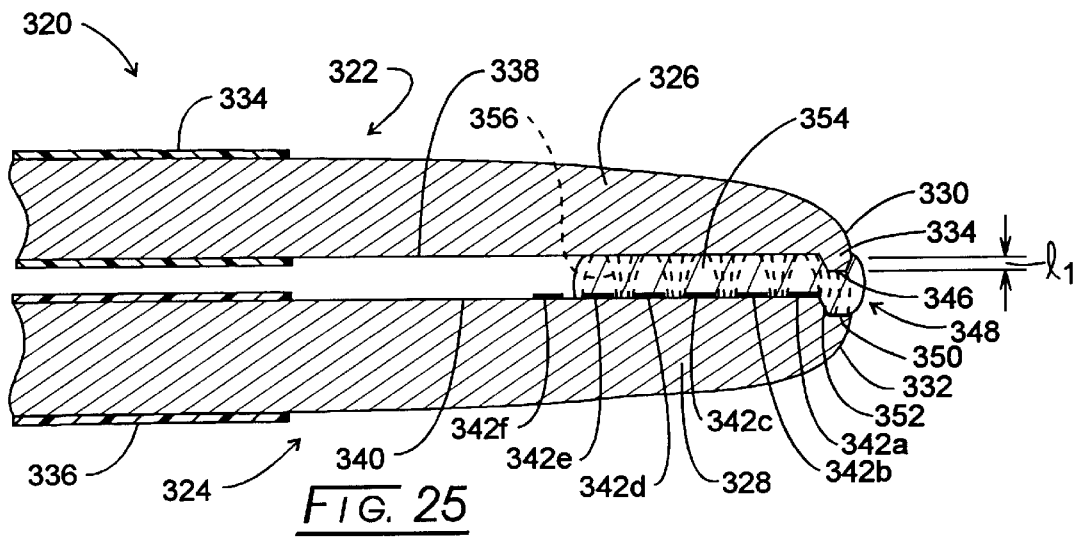
FIG. 25 is a partial sectional view of another embodiment of the invention with portions exaggerated to reveal structure.
Figure 26:
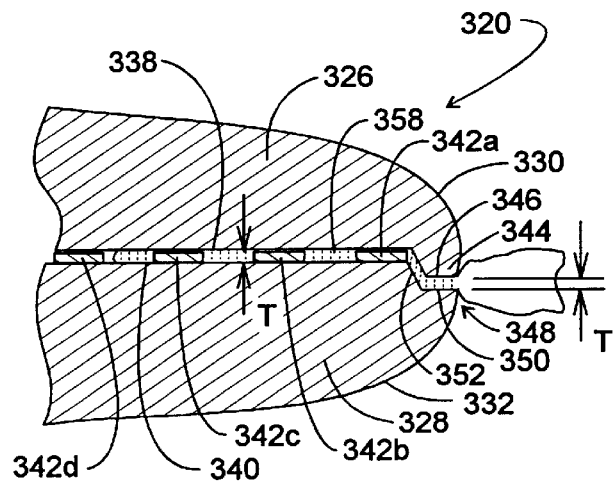
FIG. 26 is a partial sectional view of the embodiment of FIG. 25 showing relative grasping surface spacing.
Figure 26A:
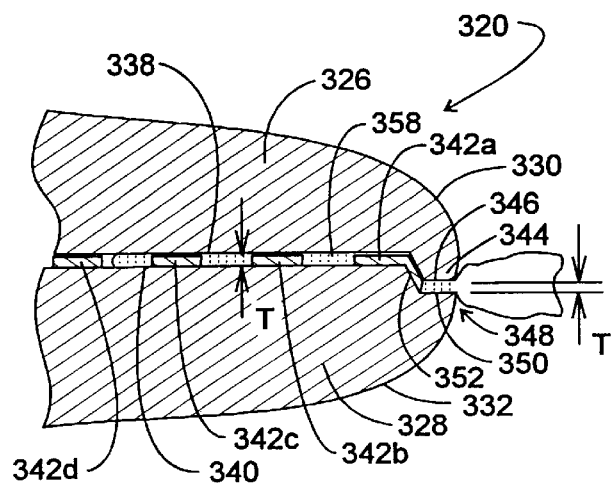
FIG. 26A is a partial sectional view of the embodiment of FIG. 25 showing an alternate arrangement or an electrically insulative spacer assembly.

The forward "snagging" tooth geometry also can be implemented in conjunction with the preferred forceps structuring discussed in conjunction with FIGS. 12. Looking to FIG. 25, such an arrangement is presented in conjunction with forceps represented generally at 320. Forceps 320 are shown having two tines 322 and 324 which extend to tip regions shown, respectively, at 326 and 328. These regions 326 and 328 are seen to respectively extend to outer or tip peripheries 330 and 332. Nylon coatings as at 334 and 336 provide electrical insulation to the respective tines 322 and 324. Forceps 320 are designed to achieve the requisite electrode spacing, T, as well as the desirable direct path or tissue confronting type path for current flux as described hereinabove. In this regard, oppositely disposed tissue grasping surfaces are provided as seen at 338 and 340. One of those surfaces, herein shown as surface 340, carries an electrically insulative spacer assembly formed as transversely disposed stripes 342a–342f. These stripes 342a–342f are provided having a thickness, T, to achieve requisite spacing. Note that tine 330 is configured having a tooth of tooth length $l_1$ with an engaging surface 346. Correspondingly, a recess 348 is formed into the tip periphery 332 and is configured having a bottom surface 350 and slanting side surface 352 to provide a geometry corresponding with that of the tooth 330. Thus, as seen in FIG. 26, with the movement of the tines 332 and 324 towards each other in a closing maneuver, the bottom surface 350 of recess 348 will be spaced from the engaging surface 346 of tooth 344 the noted distance, T. FIG. 25 shows an engagement of thicker tissue 354 with current flow paths shown in dotted fashion at 356. Note that an ideal current path configuration is achieved including the path at the tooth and recess configuration. FIG. 26 shows closure substantially to the spacing, T, over a thinner representation of tissue at 358. Looking to FIG. 26A, a variation of the embodiment of FIG. 26 is presented wherein the side surface 352 of recess 348 is coated with the spacing insulative material such as alumina. This, in effect, expands the width of stripe 342a.

Figure 27:
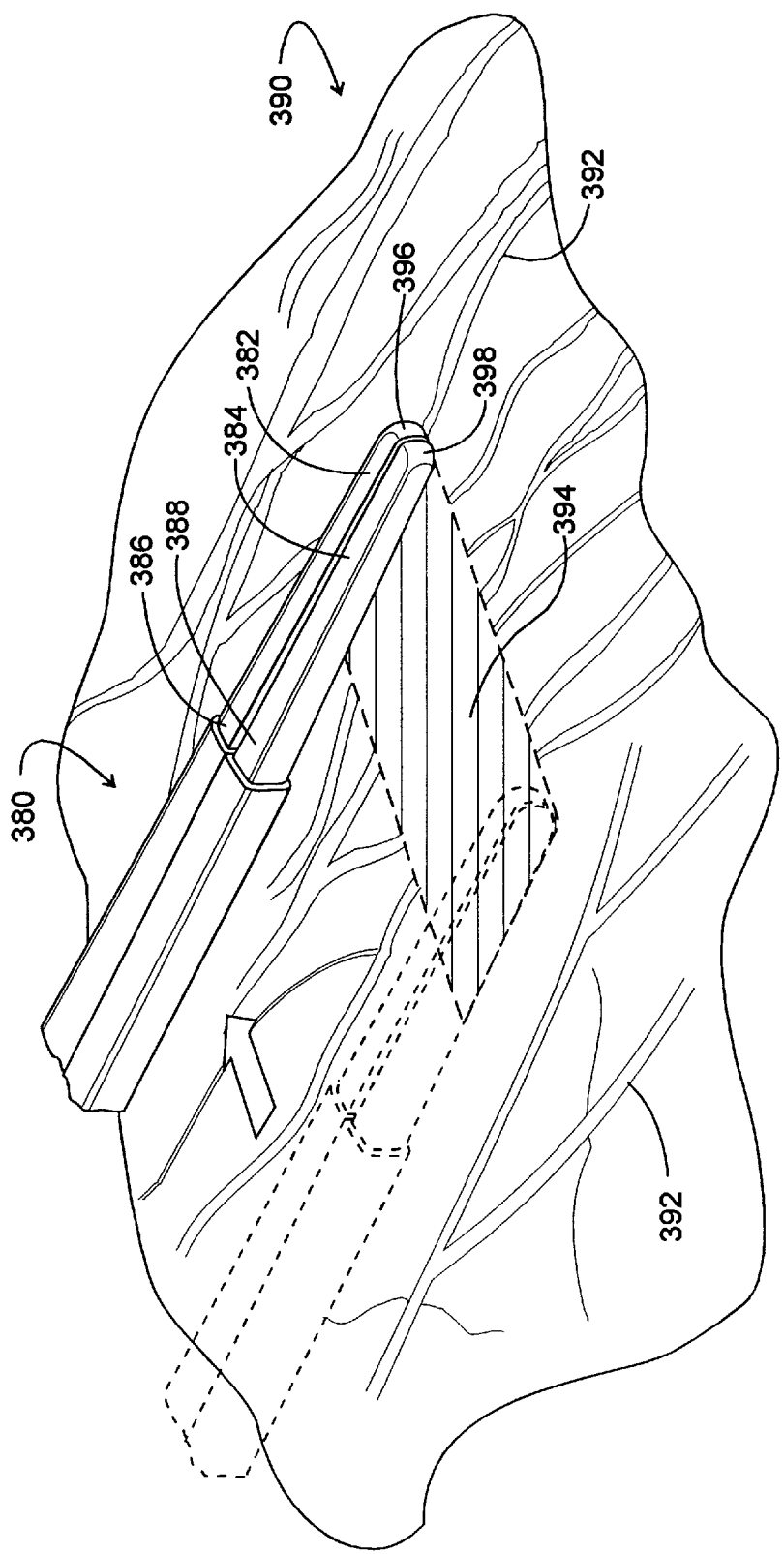
FIG. 27 is a pictorial representation of the side surface mode and method of utilization of forceps according to the invention.

Referring to FIG. 27, another modality of use of forceps according to the invention is pictorially represented. In the figure, forceps 380, as configured according to the invention, are shown being oriented such that the side surfaces of the tip regions 382 and 384 of respective tines 386 and 388 are being retained tangentially with respect to the surface of membranous tissue such as thin mesentery tissue represented in general at 390. Tissue 390 incorporates a network of small blood vessels such as seen at 392. The tissue grasping surfaces of tip regions 382 and 384 are retained in optimal spaced apart orientation by the earlier-described spacer regions (not shown) to achieve an optimal power or current density for creating a swath or path represented at 394 wherein tissue and blood vessels are efficiently coagulated. Forceps 380 also can be used to create a much smaller path of coagulation through the utilization of the blunt tips 396 and 398 of respective tip regions 382 and 384. With this "coagulative painting" modality, relatively larger areas can be efficiently coagulated prior to incision or blunt dissection using other surgical instruments.

Figure 28:
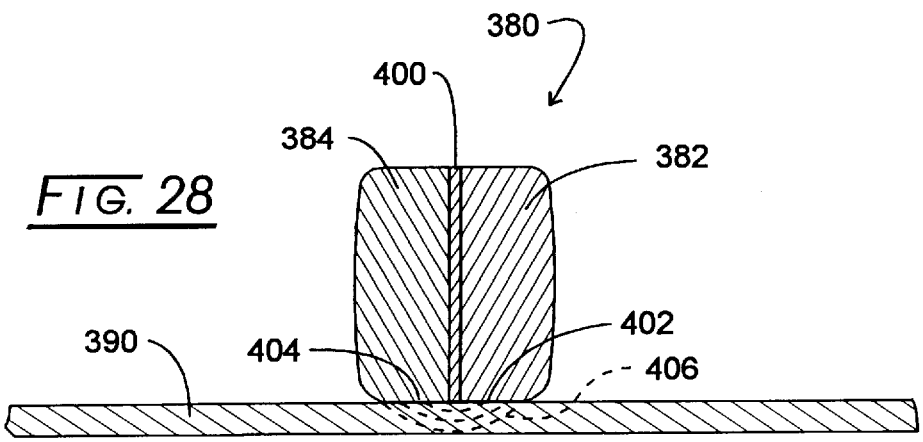
FIG. 28 is a sectional view of forceps according to the invention employed in the manner shown in FIG. 27.

These features further are depicted in connection with FIG. 28. Looking to that figure, the tip regions 382 and 384 again are represented along with a somewhat exaggerated rendition of the electrically insulative spacer region as at 400. As noted above, the cross-section of forceps according to the invention is somewhat rectangular with relatively broad side surfaces. In this regard, note that side surfaces 402 and 404 of respective tip regions 382 and 384 provide for an enlarged contact area of electrically conductive material with the surface of tissue 390. Recalling the discourse above in connection with FIG. 5 and equation (1), by enhancing the area of side surfaces 402 and 404, an improved current and power density is achieved. This area of current flow confrontation resides in the denominator of the equation-based determination of load resistance. Thus, the forceps 380 are enabled to perform at a more efficient location upon the electrosurgical generator characteristic as represented at FIG. 5. The improved current flux flow is represented at dashed lines 406 in FIG. 28. Of course, the insulative spacer region 400 achieves optimal spacing apart of the surfaces 402 and 404 to achieve this desired current density represented at 406. An additional advantage accrues with the more efficient distribution of current within the tissue 390 in that the surgeon is able to carry out this coagulative painting technique at a more rapid rate than otherwise available with conventional instruments.

Figure 29:
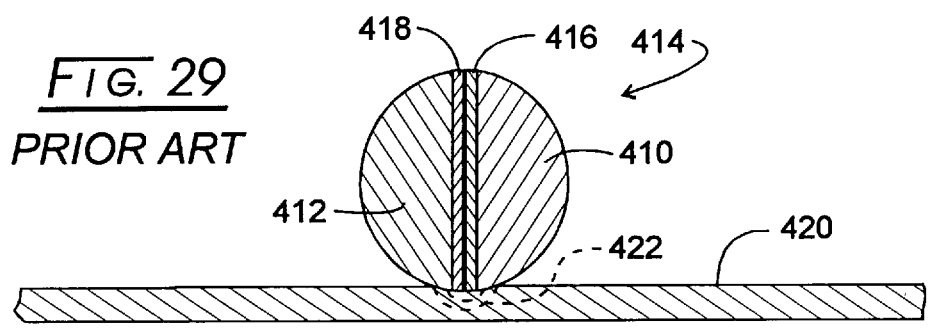
FIG. 29 is a sectional view of forceps according to the prior art being utilized in the mode shown in FIG. 27.

Comparing the representation of FIG. 28 with that at FIG. 29 demonstrates the current density based advantages of the present invention. Forceps heretofore available for the most part have cross sections corresponding with the cord of a circle as represented by the cross-sectional representation of the tip regions 410 and 412 of forceps 4314. These tip regions 410 and 412 are shown to be spaced apart by insulative spacer coatings shown, respectively, at 416 and 418. The side portions of the forceps of the tip regions 410 and 412 available to carry out coagulative painting are quite limited to achieve a current flow through the tissue. Note the limited extent of confronted area as represented by dashed current flux lines 422. This geometry does is not promote efficient coagulation and imposes a time stricture upon the surgeon inasmuch as a lengthier period of time is required to achieve requisite Joulean heating within the membrane 420 with the restricted current density generated.

Figure 30:
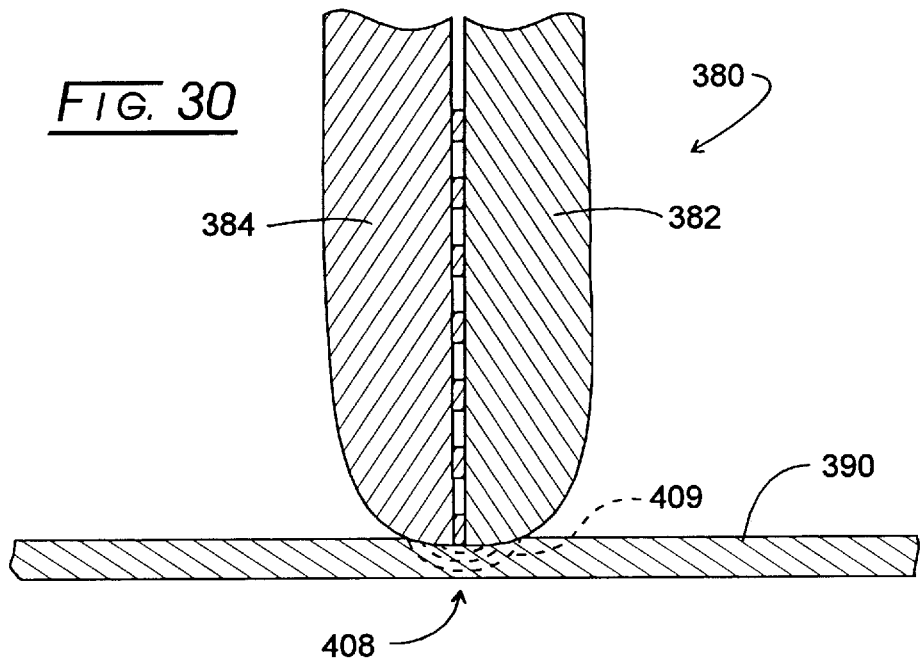
FIG. 30 is a partial sectional view of forceps according to the invention being used in another version of the mode described in connection with FIG. 27.

Referring to FIG. 30, the blunt nose or distal end of forceps 380 also may be employed for a more localized coagulative painting procedure. Because of the blunt or almost rectangular cross-sectional profile of the tip portion as seen generally at 408 of the forceps 380, adequate current densities are achieved to coagulate a small region of membrane or tissue 390. In the figure, the current flux lines are represented by dashed lines 409.

Figure 31:
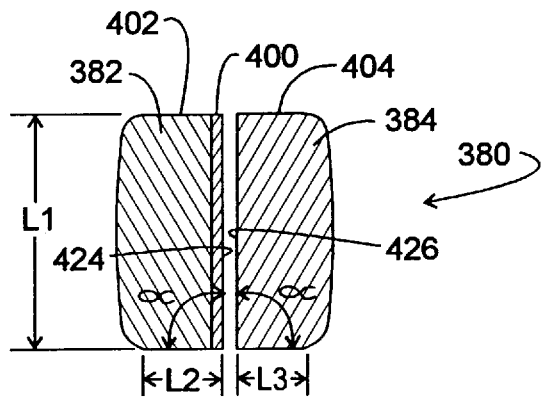
FIG. 31 is a sectional view of the tip region of forceps according to the invention for supporting a geometric analysis thereof.

Referring to FIG. 31, the geometric criteria by which the desired current densities are achieved with the side surfaces 402 and 404 as described in FIG. 28 are portrayed. In the figure, the widthwise extent of the forceps 380 are represented as the distance L1. Generally, this dimension will be about 0.040 to 0.120 inch (1.0 to 3 mm) in extent. The thickness lengths L2 and L3 shown in the figure represent that portion of the width of the side surfaces, for example as at 402 and 404, of the tip regions which is at an angle α of 80° to 100° relative to the grasping surfaces of tip regions 382 and 384 shown, respectively, at 424 and 426. Thus, the distances or dimensions L2 and L3 are the effective side surface height values which provide for effective electrical contact with the tissue engaged by the tip regions. Considering the ratios of the dimensions L1, L2, and L3, it is preferred that the ratio (aspect) of width L1 to electrical contact length L2 and, correspondingly, the ratio of the widthwise dimension L1 to the corresponding effective electrical contact length L3 be in the range from about 0.25 to 10. A preferred ratio will be about 0.4 to 5.

Figure 32:
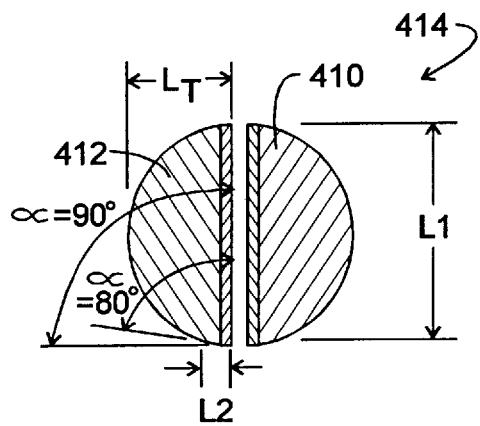
FIG. 32 is a sectional view of the tip region of forceps according to the prior art for supporting a comparative analysis with respect to FIG. 31.

Referring to FIG. 32, a comparative analysis is given with respect to the prior art structures typically encountered as described in connection with FIG. 29. In the figure, the cross section of forceps 414 is reproduced with tip regions 410 and 412. The maximum thickness of the tip regions is represented as $L_T$ and the corresponding widthwise dimension L1 is shown in the drawing. The effective electrical contact length for this prior art embodiment is shown at L2 for a value of α of 80°. Note that the effective length L2 is quite small with respect to the value L1. At a value of α of 90°, the length L2 approaches a point or line. Generally, the ratio of L1 to L2 for prior art instruments will be about 5 or more.

As discussed hereinabove, the forceps of the present invention may be used in conjunction with widely available electrosurgical generators characterized by a fixed internal impedance and fixed operating frequency which deliver maximum power to an external load (e.g., tissue) having an electrical impedance in the range of about 50 ohms to 150 ohms as discussed in conjunction with FIG. 5. In this type of bipolar electrosurgical generator, the applied voltage increases monotonically as the load impedance increases, increasing to the maximum "open circuit" voltage as the load impedance increases to levels of tens of thousands of ohms or more. In addition, forceps of the present invention may be used with bipolar electorsurgical generators having a fixed operating frequency and an output voltage which is substantially constant over a range of load impedances of tens of ohms to tens of thousands of ohms including "open circuit" conditions. Such electrosurgical generators are described in U.S. Pat. Nos. 4,969,885 and 5,472,443 which are incorporated herein by reference. Also, the forceps of the present invention may be advantageously used with bipolar electrosurgical generators of either the variable voltage design (see FIG. 5) or substantially constant voltage design described hereinabove in which the applied voltage is interrupted when the delivered current decreases below a predetermined level. Such bipolar generators are often referred to as "automatic" generators in that they sense the completion of the coagulation process and terminate the application of voltage, often accompanied by an audible indication in the form of a cessation of a "voltage application" tone or the annunciation of a unique "coagulation complete" tone.

Further, the forceps of the present invention may be used with electrosurgical generators whose operating frequency varies with the load impedance as a means to modulate the applied voltage with changes in load impedance. Such electrosurgical generators are described in U.S. Pat. Nos. 5,099,840; 5,438,302; and 5,423,810, all of which are incorporated herein by reference.

Alternatively to the provision of smooth metal surfaces on the grasping surfaces of the forceps tines to reduce sticking of tissue or coagulum, those tissue grasping surfaces (see, for example, tissue grasping surfaces 160 and 162 in FIG. 12) may be coated with an electrically conductive non-stick coating. Additionally, those surfaces may be coated with electrically insulative non-stick coating material which is sufficiently thin and/or applied to a sufficiently rough surface to provide a multiplicity of regions on the contacting surfaces which are uncoated with insulative non-stick coating material. Such non-stick coatings may include metal-filled (containing metal particles) organic materials such as fluoropolymers or other compounds generally defined as Teflon® (polytetrafluoroethylene polymers and copolymers) or thin fluoropolymers such as Vydax®, both of which are manufactured by E.I. DuPont de Nemours of Wilmington, Del. The use of such non-stick coatings which also support the conduction of high-frequency current are described in U.S. Pat. Nos. 5,549,604; 4,876,110; 4,785,807; 4,333,467 and 4,314,559, all of which are incorporated herein by reference. In addition, metallic coatings such as ME-92 (ME-92 Operations, Providence, R.I.) and MED-COAT 2000 (supra) may be applied to the stainless steel surfaces at the working end of the bipolar forceps to reduce the sticking of tissue thereto.

In addition to the construction methods described above, the forceps of the present invention may be fabricated by inserting the proximal portions of the tines into molded plastic support members or by using insert molding manufacturing process as a means to reduce the cost of manufacture. Alternatively, the metallic support members 36 and 38 shown in FIG. 1 may be made of one metal (e.g., 300 or 400 series stainless steel) and joined to a second metal in distal tip regions 40 and 42 such as tungsten or niobium. Such a construction allows the use of a metal support member offering low cost manufacture and preferred mechanical properties in combination with a metal distal tip member such as tungsten offering high thermal conductivity and/or a preferred thermal expansion coefficient for ease of joining to or deposition of the insulative strip or strips. Such dissimilar metals may be joined using methods such as welding, brazing, soldering, electrically conductive adhesives or by mechanical attachment such as riveting or threaded joining methods.

As discussed above in connection with FIG. 12A, a preferred configuration for forceps according to the invention is one wherein each of the tines of the forceps provide for thermal conduction from their tip regions to maintain the tissue grasping surfaces below, for example, a temperature of about 60° C. to 85° C. By so limiting the tip region temperatures, any tendency for sticking phenomena to occur is substantially lessened. In general, this desired temperature limitation is readily achieved for open surgical configurations by providing thermal conduction both to the thinly gloved hand of the surgeon and to the air surrounding the proximal portions of the forceps tines. Copper, exhibiting a thermal conductivity of about 3.9 watts/cm is the preferred material for this thermal conveyance. However, that material is not a biocompatible one and exhibits elasticity characteristics unsuited for the function at hand. Accordingly, a laminar composite is devised made with a layer of copper and a layer of biocompatible stainless steel which are metallurgically bonded together, for example, by roll bonding or the like. To coat the copper component of this laminar composite, a hard, generally non-sticking coating of chromium or the like may be applied, for example, the above-noted Medcoat 2000. In general, where alumina is utilized as the insulative spacer assembly, the electroplating form of coating is readily carried out after the alumina spacer assemblies have been attached with no adherence of the deposited surface material upon the alumina spacers. The union of the copper component with a stainless steel component also provides necessary stiffness to the tine structure.

Since certain changes may be made in the above apparatus without departing from the scope of the invention herein involved, it is intended that all matter contained in the above description or shown in the accompanying drawings shall be interpreted as illustrative and not in a limiting sense.

What is claimed is:

1. Surgical forceps connectable with the bipolar output of an electrosurgical generator for grasping tissue and for effecting hemostasis, comprising:

a first tine connectable with a said output of first polarity and extending longitudinally to a first tip region having an inwardly disposed electrically conductive tissue grasping surface with a first periphery of predetermined shape;

a second tine connectable with a said output of second polarity and extending longitudinally to a second tip region having an inwardly disposed electrically conductive tissue grasping surface with a periphery of predetermined shape, said first and second tip regions being mutually oppositely disposed in alignment and relatively movable from an open tankard a closed orientation for grasping said tissue; and at least two, electrically insulative, spaced apart spacer regions mounted upon at least one said grasping surface for spacing said electrically conductive surfaces apart a distance, T, when substantially in said closed orientation effective to derive a substantially uniform power density along current paths between said surfaces and through grasped tissue of length not exceeding a value achieving effective coagulation of said grasped tissue while avoiding arcing and said spacer regions having a geometry effective to securely grasp and extrude said tissue into electrically conducting contact with each interstitial contact surface adjacent said spacer regions at said grasping surfaces to derive said current paths and avoid slippage from said tissue during its surgical manipulation.

2. The surgical forceps of claim 1 in which said distance, T, is less than about 0.020 inch.

3. The surgical forceps of claim 1 in which said distance, T, is less than or equal to about 0.010 inch.

4. The surgical forceps of claim 1 in which said distance, T, has a minimum value of about 0.003 inch.

5. The surgical forceps of claim 1 in which said electrically insulative spaced apart spacer regions are parallel strips of insulative material.

6. The surgical forceps of claim 1 in which said electrically insulative spaced apart spacer regions are parallel strips of insulative material fixed to said grasping surface at said first tip region and having a thickness corresponding with said distance, T.

7. The surgical forceps of claim 6 in which:

said first tine extends to a first tip periphery of said first tip region;

said second tine extends to a second tip periphery of said second tip region;

said parallel strips of insulative material extend across the said first periphery of said grasping surface transversely to the longitudinal extent of said first tine; and one said strip of insulative material is located at said first tip periphery to provide a tissue snagging function.

8. The surgical forceps of claim 7 in which:

said first and second tip regions are formed of a thermally conductive, biologically compatible metal; and said first and second tip regions are coated with an electro-deposited biocompatible metallic layer.

9. The surgical forceps of claim 6 in which said parallel strips of insulative material extend in substantially parallel relationship with the longitudinal extent of said first tine.

10. The surgical forceps of claim 1 in which said electrically insulative spaced apart regions comprise:

a first array of parallel strips of insulative material fixed to said grasping surface at said first tip region and having a thickness, T1;

a second array of strips of insulative material fixed to said grasping surface at said second tip region, said strips thereof having a thickness, T2, and being aligned for movement into mutual contact with corresponding strips of said first array when said first and second tip regions are in a said closed orientation; and the sum of said thickness', T1 and T2 corresponds with said distance, T.

11. The surgical forceps of claim 1 in which:

said electrically insulative spaced apart spacer regions are first parallel strips of insulative material fixed to said grasping surface at said first tip region; and second parallel strips of insulative material fixed to said grasping surface at said second tip region; and said first parallel strips and second parallel strips having thicknesses deriving said distance, T.

12. The surgical forceps of claim 1 in which said electrically insulative spaced apart spacer regions are configured as an array of discrete, spaced apart cubes.

13. The surgical forceps of claim 1 in which said electrically insulative, spaced apart spacer regions are configured as an array of discrete, spaced apart circular layers.

14. The surgical forceps of claim 1 in which each said tine tip region is configured as a laminar composite having a thermally conductive component bonded with an inwardly disposed biocompatible component;

said spacer regions are deposited upon and supported by a said biocompatible component.

15. The surgical forceps of claim 14 in which said thermally conductive component is copper, said biocompatible component is stainless steel, and said spacer regions are formed of alumina.

16. The surgical forceps of claim 14 in which said composite is provided as a bonded copper and stainless steel laminate having a copper content of about 50% to 90% by volume.

17. Surgical forceps connectable with the bipolar output of an electrosurgical generator for grasping tissue and for effecting hemostasis, comprising:

a first tine connectable with said output of first polarity and extending longitudinally to a first tip region having an inwardly disposed electrically conductive metal first tissue grasping surface;

a second tine connectable with said output of second polarity and extending longitudinally to a second tip region having an inwardly disposed electrically conductive metal second tissue grasping surface, said first and second tip regions being mutually oppositely disposed in alignment and relatively movable from an open toward a closed orientation for grasping tissue; and an electrically insulative spacer assembly mounted upon said second tip region metal second tissue grasping surface and having a configuration with said first tissue grasping surface for spacing them apart a distance, T, when said first and second tines are in said closed orientation, the geometric surface shape of said configuration and said distance, T, being effective to establish electrical contact between metal tissue grasping surface exposed portions of said second tissue grasping surface at said second tip region and grasped tissue and to derive current paths defining a substantially uniform power density, between said first and second tissue grasping surfaces and through grasped tissue therebetween of lengths not exceeding a value achieving effective coagulation of said grasped tissue, said geometric surface shape being effective to securely grasp and extrude said tissue into electrically conducting contact with each said first and second tissue grasping surface.

18. The surgical forceps of claim 17 in which said electrically insulative spacer assembly spacing distance, T, has a minimum value of about 0.003 inch.

19. The surgical forceps of claim 17 in which said electrically insulative spacer assembly comprises at least one strip of insulative material fixed to said second electrically conductive metal tissue grasping surface.

20. The surgical forceps of claim 17 in which said electrically insulative spacer assembly comprises an array of spaced apart parallel strips disposed normally to the longitudinal extent of said second tine, one said strip being located at the longitudinally outermost portion of said first tissue grasping surface.

21. The surgical forceps of claim 20 in which at least one said first and second tissue grasping surface includes a portion adjacent said spacer assembly with a biocompatible surface coating formed of polytetrafluoroethylene polymer or copolymer.

22. The surgical forceps of claim 21 in which said surface coating contains metal particles.

23. The surgical forceps of claim 17 in which said electrically insulative spacer assembly comprises an array of spaced apart parallel strips disposed in parallel relationship with the longitudinal extent of said second tine.

24. The surgical forceps of claim 17 in which said electrically insulative spacer assembly is configured as an array of discrete spaced apart cubes.

25. The surgical forceps of claim 17 in which said electrically insulative spacer assembly is configured as an array of discrete spaced apart circular layers.

26. The surgical forceps of claim 17 in which at least one of said first and second tissue grasping surfaces includes a portion adjacent said spacer assembly with a biocompatible surface coating formed of a polytetrafluoroethylene polymer or copolymer.

27. The surgical forceps of claim 26 in which said biocompatible surface coating contains metal particles.

28. The surgical forceps of claim 17 in which each said tine tip region is configured as a laminar composite having a thermally conductive component bonded with an inwardly disposed biocompatible component;

said spacer assembly is deposited upon and supported by a said biocompatible component.

29. The surgical forceps of claim 28 in which said thermally conductive component is copper, said biocompatible component is stainless steel, and said spacer assembly is formed of alumina.

30. The surgical forceps of claim 28 in which said composite is provided as a bonded copper and stainless steel laminate having a copper content of about 50% to 90% by volume.

31. Surgical forceps connectable with the bipolar output of an electrosurgical generator having a power output to load impedance characteristic exhibiting a preferred load impedance range for effecting hemostasis of grasped tissue, comprising:

a first tine connectable with said output of first polarity and extending longitudinally to a first tip region having an inwardly disposed electrically conductive first tissue grasping surface with a first periphery of predetermined shape;

a second tine connectable with said output of second polarity and extending longitudinally to a second tip region having an inwardly disposed electrically conductive second tissue grasping surface with a second periphery of predetermined shape, said first and second tip regions being mutually oppositely disposed in alignment and relatively movable from an open toward a closed orientation for grasping tissue; and an electrically insulative spacer assembly fixed to at least one said first and second tissue grasping surface and having a configuration for spacing said first and second grasping surfaces apart a distance, T, when said first and second tines are in said closed orientation, said distance, T, and the surface configuration of said spacer assembly being selected to derive a load impedance with respect to said grasped tissue within said desired load impedance range when said first and second grasping surfaces are grasping tissue while spaced apart substantially about said distance, T, said configuration being effective to derive current paths between said first and second grasping surfaces corresponding with said load impedance and said spacer assembly, having a geometry effective to securely grasp and extrude said tissue into electrically conducting contact with each interstitial contact surface adjacent said spacer assembly at said grasping surfaces to derive said current paths and avoid slippage from said tissue during its surgical manipulation.

32. The surgical forceps of claim 31 in which said electrically insulative spacer assembly spacing distance, T, has minimum value of about 0.003 inch.

33. The surgical forceps of claim 31 in which said electrically insulative spacer assembly comprises at least one strip of insulative material fixed to said first tissue grasping surface at the outermost periphery of said first tip region longitudinal extent.

34. The surgical forceps of claim 39 in which said electrically insulative spacer assembly comprises an array of spaced apart parallel strips located upon said first tissue grasping surface and disposed normally to the longitudinal extent of said first tine.

35. The surgical forceps of claim 31 in which said electrically insulative spacer assembly comprises an array of spaced apart parallel strips located upon said first tissue grasping surface and disposed in parallel relationship with the longitudinal extent of said first tine.

36. The surgical forceps of claim 31 in which said electrically insulative spacer assembly is configured as an array of discrete spaced apart cubes.

37. The surgical forceps of claim 31 in which said electrically insulative spacer assembly is configured as an array of discrete spaced apart circular layers.

38. The surgical forceps of claim 31 in which:

said first tine first tip region is of generally rectangular cross-section, one surface of which is said first tissue grasping surface having a width, L1, transverse to the longitudinal extent of said first tine and having a first side surface of an effective length, L2, disposed at an angle, α, with respect to said first tissue grasping surface;

said second tine second tip region is of generally rectangular cross-section, one surface of which is said second tissue grasping surface having a width, L1, transverse to the longitudinal extent of said second tine and having a second side surface of an effective length, L3, disposed at said angle, α with respect to said second tissue grasping surface; and said angle, α is selected from within a range of between about 80° and 100° establishing adjacent said first and second side surfaces at respective said first and second tip regions having said effective lengths L2 and L3 with values effective to provide hemostasis in tissue when in sliding contact with them, said effective lengths L2 and L3 having values selected to evoke load impedances substantially within said preferred impedance range.

39. The surgical forceps of claim 38 the ratio of said width L1, to each said effective lengths L2 and L3 is within a range of about 0.25 to 10.

40. The surgical forceps of claim 31 in which each said tine tip region is configured as a laminar composite having a thermally conductive component bonded with an inwardly disposed biocompatible component;

said spacer regions are deposited upon and supported by a said biocompatible component.

41. The surgical forceps of claim 40 in which said thermally conductive component comprises copper, said biocompatible component comprises stainless steel, and said spacer assembly comprises alumina.

42. The surgical forceps of claim 40 in which said composite is provided as a bonded copper and stainless steel laminate having a copper content of about 50% to 90% by volume.

43. Surgical forceps connectable with the bipolar output of an electrosurgical generator for contacting tissue to effect hemostasis, said generator exhibiting a given power output to load impedance characteristic having an impedance range of efficient coagulation performance comprising:

a first tine connectable with a said output of first polarity and extending longitudinally to a first tip region of generally rectangular cross-section, one surface of which is an inwardly disposed electrically conductive tissue grasping surface having a width, L1, transverse to said longitudinal extent and having a first side surface of an effective length, L2, disposed at an angle, α with respect to said tissue grasping surface;

a second tine connectable with a said output of second polarity and extending longitudinally to a second tip region of generally rectangular cross-section and one surface of which is an inwardly disposed electrically conductive tissue grasping surface having a said width, L1, transverse to said longitudinal extent and having a second side surface of an effective length, L3, disposed at said angle, α with respect to said tissue grasping surface of said second tip region, said first and second tip regions and said first and second side surfaces being mutually oppositely disposed in substantial alignment and said first and second tip regions being relatively movable from an open toward a closed orientation for grasping said tissue;

an electrically insulative spacer assembly fixed to at least one said tissue grasping surface for spacing said electrically conducting tissue grasping surfaces apart a distance, T, when said first and second tines substantially are in said closed orientation; and said angle, α is selected from within a range between about 80° and 100° establishing adjacent said first and second side surfaces at respective said first and second tip regions having said effective lengths L2 and L3 with values effective to provide hemostasis in tissue in sliding contact with them, said effective lengths. L2 and L3, having values selected to evoke load impedances substantially within said impedance range.

44. The surgical forceps of claim 43 in which the ratio of said width, L1, to each said effective lengths L2 and L3 is within a range of about 0.25 to 10.

45. The surgical forceps of claim 43 in which the ratio of said width L1, to each said effective lengths L2 and L3 is within a range of about 0.4 to 5.

46. The surgical forceps of claim 43 in which said electrically insulative spacer assembly has a configuration to provide said distance, T, at a value effective to establish electrical contact between the exposed portions of said metal tissue grasping surfaces and tissue grasped thereby to derive current paths defining a substantially uniform power density between said tissue grasping surfaces and through grasped tissue therebetween of length not exceeding a value achieving effective coagulation of said grasped tissue.

47. The surgical forceps of claim 46 in which said distance, T, has a minimum value of about 0.003 inch.

48. The method for grasping a select component of tissue of a body and effecting hemostasis at such tissue comprising the steps of:

provedig an electrosurgical generator controllable to have a bipolar output;

providing surgical forceps, including:

a first tine connectable with said output of first polarity and extending longitudinally to a first tip region having an inwardly disposed electrically conductive metal first tissue grasping surface, a second tine connectable with said output and extending longitudinally to a second tip region having an inwardly disposed electrically conductive metal second tissue grasping surface, said first and second tip regions being mutually oppositely disposed in alignment and relatively movable from an open toward a closed orientation for grasping tissue, and an electrically insulative spacer assembly mounted upon at least one said first and second tissue grasping surface and having a configuration for spacing them apart a distance, T, when said first and second tines substantially are in said closed orientation, the geometric surface shape of said configuration and said distance, T, being effective to derive current paths defining a substantially uniform power density between said surfaces and through grasped tissue of lengths not exceeding a value achieving effective coagulation of said grasped tissue while avoiding arcing, said geometric surface shape being effective to securely grasp and extrude said tissue into electrically conducting contact with each said grasping surface;

grasping said component of tissue between said first and second tip regions by manually urging said first and second tines toward said closed orientation such that said component of tissue is extruded into contact with said metal first tissue grasping surface and said second metal tissue grasping surface to an extent said length is substantially derived; and controlling said electrosurgical generator to convey current from said output to said first and second tines to establish current flow along said current path for an interval effective to establish said hemostasis.

49. The method of claim 48 in which said electrically insulative spacer assembly configuration provides said distance, T, as having a value less than about 0.020 inch.

50. The method of claim 48 in which said electrically insulative spacer assembly configuration provides said distance, T, as having a value less than or equal to about 0.010 inch.

51. The method of claim 48 in which said electrically insulative spacer assembly configuration provides a distance, T, as having a minimum value of about 0.003 inch.

52. The method of claim 48 in which:

said electrosurgical generator is provided having a power output to load impedance characteristic exhibiting a preferred load impedance range for effecting hemostasis of said tissue component; and said electrically insulated spacer assembly established distance, T, is effective to derive said current path between said first and second tissue grasping surfaces and through said tissue component of length not exceeding a value achieving effective coagulation of said grasped tissue and establishing a load impedance through said grasped tissue within said preferred load impedance range.

53. The method of claim 48 in which said electrically insulative spacer assembly is provided as parallel strips of insulative material fixed to at least one said first and second tissue grasping surface.

54. The method for effecting hemostasis at the surface of tissue comprising the steps of:

providing an electrosurgical generator controllable to have an output, said generator exhibiting a given power output to load impedance characteristic having an impedance range of efficient coagulation performance;

providing surgical forceps, including:

a first tine connectable with said output and extending longitudinally to a first tip region of generally rectangular cross-section, one surface of which is an inwardly disposed electrically conductive tissue grasping surface having a width, L1, transverse to said longitudinal extent and having a first side surface of an effective length, L2, disposed at an angle, α, with respect to said tissue grasping surface, a second tine connectable with said output and extending longitudinally to a second tip region of generally rectangular cross-section and one surface of which is an inwardly disposed electrically conductive tissue grasping surface, having a said width, L1, transverse to said longitudinal extent and having a second side surface of an effective length, L3, disposed at said angle, α, with respect to said tissue grasping surface of said second tip region, said first and second tip regions and said first and second side surfaces being mutually oppositely disposed in substantial alignment and said first and second tip regions being relatively movable from an open toward a closed orientation for grasping said tissue, an electrically insulative spacer assembly fixed to at least one said tissue grasping surface for spacing said electrically conducting tissue grasping surfaces apart a distance, T, when said first and second tines substantially are in closed orientation, and said angle, α, is selected from within a range between about 80° and 100° establishing adjacent said first and second side surfaces at respective said first and second tip regions having said effective lengths L2 and L3 with values effective to provide hemostasis in tissue in sliding contact with them said effective lengths, L2 and L3 having values selected to evoke load impedances substantially within said impedance range;

manually moving said first and second tines substantially into said closed orientation;

contacting said surface simultaneously with said first and second side surfaces while said first and second tines are substantially in said closed orientation;

controlling said electrosurgical generator to convey current from said output to said first and second tines to establish a flow of current from said first side surface, through said tissue to said second side surface to effect said hemostasis; and moving said forceps to deliver said effected hemostasis along a predetermined path while said first and second tines are substantially in said closed orientation and said flow of current is established.

55. The method of claim 54 in which said surgical forceps are provided wherein the ratio of said width, L1, to each said effective lengths L2 and L3 is within a range of about 0.25 to 10.

56. The method of claim 54 in which said surgical forceps are provided wherein the ratio of said width, L1, of said effective lengths, L2 and L3, is within a range of about 0.4 to 5.

57. The method of claim 54 in which said electrically insulative spacer assembly provides said distance, T, as having a value less than about 0.020 inch.

58. The method of claim 54 in which said electrically insulative spacer assembly provides said distance, T, as having a value less than or equal to about 0.010 inch.

59. The method of claim 54 in which said electrically insulative spacer assembly provides a distance, T, as having a minimum value of about 0.003 inch.

60. Surgical forceps connectable with the output of an electrosurgical generator for grasping tissue and for effecting hemostasis, comprising:

a first tine connectable with said output and extending longitudinally to a first tip region, said first tip region being a first laminar composite having a first thermally conductive outwardly disposed metal component bonded with a first biocompatible, electrically conductive metal inwardly disposed component configured to provide a first tissue grasping region, a second tine connectable with said output and extending longitudinally to a second tip region, said second tip region being a second laminar component having a second thermally conductive outwardly disposed metal component bonded with a second biocompatible electrically conductive metal inwardly disposed component configured to provide a second tissue grasping region, said first and second tip regions being mutually oppositely disposed in alignment and relatively movable from an open toward a closed orientation for grasping tissue; and an electrically insulative spacer assembly mounted upon at least one said first and second tissue grasping region respective first and second biocompatible electrically conductive metal component and having a configuration for spacing them apart a distance, T, when said firs and second tines are in said closed orientation, the geometric surface shape of said configuration, and said distance, T, being effective to derive a substantially uniform power density along current paths between said first an second regions and through grasped tissue of length not exceeding a value achieving effective coagulation of said grasped tissue while avoiding arcing, and said spacer assembly, having a geometry effective to securely grasp and extrude said tissue into electrically conducting contact with each interstitial contact surface adjacent said spacer assembly at said grasping regions to derive said current paths and avoid slippage from said tissue during its surgical manipulation.

61. The surgical forceps of claim 60 in which said first and second thermally conductive metal components comprise copper and said first and second biocompatible electrically conductive components comprise stainless steel.

62. Surgical forceps connectable with the bipolar output of an electrosurgical generator for grasping tissue and for effecting hemostasis, comprising:

a first tine connectable with said output of first polarity and extending longitudinally to a first tip region having an inwardly disposed electrically conductive metal first tissue grasping surface;

a second tine connectable with said output of second polarity and extending longitudinally to a second tip region having an inwardly disposed second electrically conductive metal tissue grasping surface, said first and second tip regions being mutually oppositely disposed in alignment and relatively movable from an open toward a closed orientation for grasping tissue; and an electrically insulative spacer assembly mounted upon at least one said first and second tip region metal tissue grasping surface and having a configuration for spacing them apart a distance, T, when said first and second tines are in said closed orientation, said distance, T, being limited to an extent effective to cause the extrusion of said tissue into intimate electrical contact with each said first and second tissue grasping surfaces when said first and second tip regions are moved toward said closed orientation to define current paths between said first and second tissue grasping surfaces and through grasped tissue therebetween deriving uniform power density and achieving effective coagulation of said grasped tissue.

63. The surgical forceps of claim 62 in which said electrically insulative spacer assembly spacing distance, T, has a minimum value of about 0.003 inch.

64. The surgical forceps of claim 62 in which said electrically insulative spacer assembly comprises at least one strip of insulative material fixed to a said first or second electrically conductive metal tissue grasping surface.

65. The surgical forceps of claim 62 in which said electrically insulative spacer assembly comprises an array of spaced apart parallel strips disposed normally to the longitudinal extent of a said first or second tine upon which it is mounted, one of said strips being located at the longitudinally outermost portion of said first tissue grasping surface.

66. The surgical forceps of claim 62 in which said electrically insulative spacer assembly comprises an array of spaced apart parallel strips disposed in parallel relationship with the longitudinal extent of a said first or second tine upon which it is mounted.

67. Surgical forceps connectable with the bipolar output of an electrosurgical generator for grasping tissue and for effecting hemostasis, comprising:

a first tine connectable with a said output of first polarity and extending longitudinally to a first tip region having an inwardly disposed electrically conductive tissue grasping surface with a first periphery of predetermined shape and configured to provide said electrically conductive surface as a first array of sequentially disposed grooves and lands;

a second tine connectable with a said output of second polarity and extending longitudinally to a second tip region having an inwardly disposed electrically conductive tissue grasping surface with a periphery of predetermined shape, said first and second tip regions being mutually oppositely disposed in alignment and relatively movable from an open toward a closed orientation for grasping said tissue, and said second tip region being configured to provide said electrically conductive surface as a second array of sequentially disposed grooves and lands displaced along the longitudinal extent of said second tine with respect to said first array an amount effective to align each said groove of said first array with a corresponding said land of said second array; and at least two, electrically insulative, spaced apart spacer regions mounted upon at least one said grasping surface for spacing said electrically conductive surfaces apart a distance, T, when substantially in said closed orientation effective to derive a current path between said surfaces and through grasped tissue of length not exceeding a value achieving effective coagulation of said grasped tissue while avoiding arcing, said spacer regions being located only within the said grooves of said second array.

68. Surgical forceps connectable with the bipolar output of an electrosurgical generator for grasping tissue and for effecting hemostasis, comprising:

a first tine connectable with a said output of first polarity and extending longitudinally to a first tip region having an inwardly disposed electrically conductive tissue grasping surface with a first periphery of predetermined shape, said first tip region being configured having an array of discrete, spaced apart holes of circular peripheral shape;

a second tine connectable with a said output of second polarity and extending longitudinally to a second tip region having an inwardly disposed electrically conductive tissue grasping surface with a periphery of predetermined shape, said first and second tip regions being mutually oppositely disposed in alignment and relatively movable from an open toward a closed orientation for grasping said tissue; and at least two, electrically insulative, spaced apart spacer regions provided as discrete pegs mounted within said spaced apart holes and spacing said electrically conductive surfaces apart a distance, T, when substantially in said closed orientation, effective to derive a current path between said surfaces and through grasped tissue of length not exceeding a value achieving effective coagulation of said grasped tissue while avoiding arcing.

69. Surgical forceps connectable with the bipolar output of an electrosurgical generator for grasping tissue and for effecting hemostasis, comprising:

a first tine connectable with a said output of first polarity and extending longitudinally to a first tip region having an inwardly disposed electrically conductive tissue grasping surface with a first periphery of predetermined shape and extending to a first tip periphery, and including an inwardly depending tooth located at said tip periphery and having a predetermined tooth length;

a second tine connectable with a said output of second polarity and extending longitudinally to a second tip region having an inwardly disposed electrically conductive tissue grasping surface with a periphery of predetermined shape and extending to a second tip periphery, including a recess at said tip periphery extending to a bottom surface at a depth corresponding with said predetermined tooth length having a configuration corresponding with said tooth, said first and second tip regions being mutually oppositely disposed in alignment and relatively movable from an open toward a closed orientation for grasping said tissue;

an electrically insulative, spaced apart spacer region mounted upon at least one said grasping surface for spacing said electrically conductive surfaces apart a distance, T, when substantially in said closed orientation effective to derive a current path between said surfaces and through grasped tissue of length not exceeding a value achieving effective coagulation of said grasped tissue while avoiding arcing; and said bottom surface of said second tip region being spaced in electrically insulative relationship from said tooth said distance, T, in the presence of said substantially closed orientation.

70. Surgical forceps connectable with the bipolar output of an electrosurgical generator for grasping tissue and for effecting hemostasis, comprising:

a first tine connectable with a said output of first polarity and extending longitudinally to a first tip region configured as a laminar composite having a thermally conductive component bonded with an inwardly disposed biocompatible component, said first tip region having an inwardly disposed electrically conductive tissue grasping surface with a first periphery of predetermined shape;

a second tine connectable with a said output of second polarity and extending longitudinally to a second tip region configured as a laminar composite having a thermally conductive component bonded with an inwardly disposed biocompatible component, said second tip region having an inwardly disposed electrically conductive tissue grasping surface with a periphery of predetermined shape, said first and second tip regions being mutually oppositely disposed in alignment and relatively movable from an open toward a closed orientation for grasping said tissue; and at least two electrically insulative, spaced apart spacer regions deposited upon and supported by at least one said biocompatible component for spacing said electrically conductive surfaces apart a distance, T, when substantially in said closed orientation effective to derive a current path between said surfaces and through grasped tissue of length not exceeding a value achieving effective coagulation of said grasped tissue while avoiding arcing; and said composite being coated with an electro-deposited biocompatible metallic layer to provide said grasping surfaces.

71. Surgical forceps connectable with the output of an electrosurgical generator for grasping tissue and for effecting hemostasis, comprising:

a first tine connectable with said output and extending longitudinally to a first tip region having an inwardly disposed electrically conductive metal first tissue grasping surface;

a second tine connectable with said output and extending longitudinally to a second tip region having an inwardly disposed second electrically conductive metal tissue grasping surface, and configured having an array of discrete, spaced apart holes of circular peripheral shape, said first and second tip regions being mutually oppositely disposed in alignment and relatively movable from an open toward a closed orientation for grasping tissue; and an electrically insulative spacer assembly mounted upon said second tip region metal tissue grasping surface comprising discrete pegs mounted within said spaced apart holes and extending outwardly from said second electrically conductive metal tissue grasping surface, and having a configuration with said first tissue grasping surface for spacing them apart a distance, T, when said first and second tines are in said closed orientation, the geometric surface shape of said configuration and said distance, T, being effective to establish electrical contact between metal tissue grasping surface exposed portions of said second surface at said second tip region and grasped tissue and to derive a current path between said first and second tissue grasping surfaces and through grasped tissue therebetween of length not exceeding a value achieving effective coagulation of said grasped tissue.

72. Surgical forceps connectable with the output of an electrosurgical generator for grasping tissue and for effecting hemostasis comprising:

a first tine connectable with said output and extending longitudinally to a first tip region having a tip periphery and an inwardly disposed electrically conductive metal first tissue grasping surface, and including an inwardly depending tooth located at said tip periphery and having a predetermined tooth length extending to an engaging surface;

a second tine connectable with said output and extending longitudinally to a second tip region having a tip periphery and an inwardly disposed second electrically conductive metal tissue grasping surface, including a recess extending a length corresponding with said predetermined tooth length to a bottom surface and configured in correspondence with said tooth, said first and second tip regions being mutually oppositely disposed in alignment and relatively movable from an open toward a closed orientation for grasping tissue; and an electrically insulative spacer assembly comprising an insulative coating located at said recess bottom surfaced having a thickness for spacing said engaging surface from said bottom surface a distance, T, when said first and second tines are in said closed orientation, said distance, T, being effective to establish electrical contact between metal tissue grasping surface exposed portions of said second surface at said second tip region and grasped tissue and to derive a current path between said first and second tissue grasping surfaces and through grasped tissue therebetween of length not exceeding a value achieving effective coagulation of said grasped tissue.

73. Surgical forceps connectable with the output of an electrosurgical generator for grasping tissue and for effecting hemostasis, comprising:

a first tine connectable with said output and extending longitudinally to a first tip region having a tip periphery and an inwardly disposed electrically conductive metal first tissue grasping surface and including an inwardly depending tooth located at said tip periphery and having a predetermined tooth length extending to a tooth end;

a second tine connectable with said output and extending longitudinally to a second tip region having a tip periphery and an inwardly disposed second electrically conductive metal tissue grasping surface including a recess extending to a bottom surface at a depth corresponding, with said predetermined tooth length, said first and second tip regions being mutually oppositely disposed in alignment and relatively movable from an open toward a closed orientation for grasping tissue; and an electrically insulative spacer assembly mounted upon said second tip region metal tissue grasping surface and having a configuration spacing said tooth end from said bottom surface a distance, T, when said first and second tines are in said closed orientation, the geometric surface shape of said configuration and said distance, T, being effective to establish electrical contact between metal tissue grasping surface exposed portions of said second surface at said second tip region and grasped tissue and to derive a current path between said first and second tissue grasping surfaces and through grasped tissue therebetween of length not exceeding a value achieving effective coagulation of said grasped tissue.

74. Surgical forceps connectable with the output of an electrosurgical generator having a power output to load impedance characteristic exhibiting a preferred load impedance range for effecting hemostasis of grasped tissue, comprising:

a first tine connectable with said output and extending longitudinally to a first tip region having an inwardly disposed electrically conductive first tissue grasping surface with a first periphery of predetermined shape extending to a tip periphery and including an inwardly depending tooth located in said tip periphery and having a predetermined tooth length extending to an engaging surface;

a second tine connectable with said output and extending longitudinally to a second tip region having an inwardly disposed electrically conductive second tissue grasping surface with a second periphery of predetermined shape, extending to a tip periphery, including a recess extending a length corresponding with said predetermined length to a bottom surface and configured in correspondence with said tooth, said first and second tip regions being mutually oppositely disposed in alignment and relatively movable from an open toward a closed orientation for grasping tissue; and an electrically insulative spacer assembly fixed to at least one said first and second tissue grasping surface comprising an insulative coating located at said recess bottom surface having a thickness for spacing said engaging surface from said bottom surface a distance, T, when said first and second tines are in said closed orientation, said distance, T, and the surface configuration of said spacer assembly being selected to derive a load impedance within said desired load impedance range when said first and second grasping surfaces are grasping tissue while spaced apart substantially about said distance, T.

75. Surgical forceps connectable with the output of an electrosurgical generator having a power output to load impedance characteristics exhibiting a preferred load impedance range for effecting hemostasis of grasped tissue, comprising:

a first tine connectable with said output and extending longitudinally to a first tip region having an inwardly disposed electrically conductive first tissue grasping surface with a first periphery of predetermined shape, extending to a tip periphery and including an inwardly depending tooth located at said tip periphery having a predetermined tooth length extending to a tooth end;

a second tine connectable with said output and extending longitudinally to a second tip region having and an inwardly disposed electrically conductive second tissue grasping surface with a second periphery of predetermined shape, extending to a tip periphery and including a recess extending to a bottom surface at a depth corresponding with said predetermined tooth length;

said first and second tip regions being mutually oppositely disposed in alignment and relatively movable from an open toward a closed orientation for grasping tissue; and an electrically insulative spacer assembly fixed to at least one said first and second tissue grasping surface and having a configuration for spacing said tooth end from said bottom surface a distance, T; when said first and second tines are in said closed orientation, said distance, T, and the surface configuration of said spacer assembly being selected to derive a load impedance within said desired load impedance range when said first and second grasping surfaces are grasping tissue while spaced apart substantially about said distance, T.

76. Surgical forceps connectable with the output of an electrosurgical generator having a power output to load impedance characteristic exhibiting a preferred load impedance range for effecting hemostasis of grasped tissue, comprising:

a first tine connectable with said output and extending longitudinally to a first tip region having an inwardly disposed electrically conductive first tissue grasping surface with a first periphery of predetermined shape, said first tip region being configured as a laminar composite having a thermally conductive component bonded with an inwardly disposed biocompatible component;

a second tine connectable with said output and extending longitudinally to a second tip region having an inwardly disposed electrically conductive second tissue grasping surface with a second periphery of predetermined shape, said second tip region being configured as a laminar composite having a thermally conductive component bonded with an inwardly disposed biocompatible component, said first and second tip regions being mutually oppositely disposed in alignment and relatively movable from an open toward a closed orientation for grasping tissue;

an electrically insulative spacer assembly fixed to at least one said first and second tissue grasping surface at said biocompatible component and having a configuration for spacing said first and second grasping surfaces apart a distance, T, when said first and second tines are in said closed orientation, said distance, T, and the surface configuration of said spacer assembly being selected to derive a load impedance within said desired load impedance range when said first and second grasping surfaces are grasping tissue while spaced apart substantially about said distance, T; and said composite being coated with an electro-deposited biocompatible metallic layer.

77. The surgical forceps of claim 76 in which said electrically insulative spacer assembly is an alumina deposit.

78. Surgical forceps connectable with the output of an electrosurgical generator for grasping tissue and for effecting hemostasis, comprising:

a first tine connectable with said output and extending longitudinally to a first tip region, said first tip region being a first laminar composite having a first thermally conductive outwardly disposed copper metal component bonded with a first biocompatible, electrically conductive stainless steel metal inwardly disposed component configured to provide a first tissue grasping region;

a second tine connectable with said output and extending longitudinally to a second tip region, said second tip region being a second laminar component having a second thermally conductive outwardly disposed copper metal component bonded with a second biocompatible, electrically conductive stainless steel metal inwardly disposed component configured to provide a second tissue grasping region, said first and second tip regions being mutually oppositely disposed in alignment and relatively movable from an open toward a closed orientation for grasping tissue;

an electrically insulative spacer assembly mounted upon at least one said first and second tissue grasping region first and second biocompatible electrically conductive metal component and having a configuration for spacing them apart a distance, T, when said first and second tines are in said closed orientation, the geometric surface shape of said configuration and said distance, T, being effective to derive current paths between said first and second regions and through grasped tissue of length not exceeding a value achieving effective coagulation of said grasped tissue while avoiding arcing; and each said first and second laminar composites being coated with an electro-deposited layer of biocompatible metal.

79. Surgical forceps connectable with the bipolar output of an electrosurgical generator for grasping tissue and for effecting hemostasis, comprising:

a first tine connectable with said output of first polarity and extending longitudinally to a first tip region having an inwardly disposed electrically conductive metal first tissue grasping surface extending to an outer tip periphery of said first tip region;

a second tine connectable with said output of second polarity and extending longitudinally to a second tip region having an inwardly disposed second electrically conductive metal tissue grasping surface, extending to an outer tip periphery said first and second tip regions being mutually oppositely disposed in alignment and relatively movable from an open toward a closed orientation for grasping tissue; and an electrically insulative spacer assembly mounted upon said first tip region metal tissue grasping surface including a first array of parallel strips of insulative material fixed to said first tissue grasping surface at said first tip region, extending transversely to the longitudinal extent of said first tine, one said strip of insulative, material being located at said outer periphery of said first tip, said first array of parallel strips having a configuration with respect to said second grasping surface for spacing them apart a distance, T, when said first and second tines are in said closed orientation, said distance, T, being effective to establish electrical contact between metal tissue grasping surface exposed portions of said first surface at said first tip region and grasped tissue and to define a substantially uniform power density between said first and second tissue grasping surfaces and through grasped tissue therebetween achieving effective coagulation of said grasped tissue, said array of strips being effective to securely grasp and extrude said tissue into electrically conducting contact with each said first and second grasping surface; and said first and second tissue grasping surface being coated with an electro-deposited biocompatible metallic layer.

80. The surgical forceps of claim 79 in which said spacer assembly includes a second array of parallel strips of insulative material fixed to said second tissue grasping surface.

81. The surgical forceps of claim 79 in which said electrically insulative spacer assembly spacing distance, T, has a minimum value of about 0.003 inch.

82. The surgical forceps of claim 79 in which:

said generator exhibits given power output to load impedance characteristics having an impedance range of efficient coagulation performance;

said first tine first tip region is of generally rectangular cross-section, one surface of which is said first tissue grasping surface having a width, L1, transverse to the longitudinal extent of said first tine and having a first side surface of an effective length, L2, disposed at an angle, α, with respect to said first tissue grasping surface;

said second tine second tip region is of generally rectangular cross-section, one surface of which is said second tissue grasping surface having a width, L1, transverse to the longitudinal extent of said second tine and having a second side surface of an effective length, L3, disposed at said angle α, with respect to said second tissue grasping surface;

said angle, α, is selected from within a range of between about 80° and 100° establishing adjacent said first and second side surfaces at respective said first and second tip regions having said effective lengths L2 and L3 with values effective to provide hemostasis in tissue when in sliding contact with them; and said effective lengths L2 and L3 have values selected to evoke load impedances substantially within said impedance range.

83. The surgical forceps of claim 79 in which said biocompatible layer comprises a surface coating formed of polytetrafluoroethylene polymer or copolymer.

84. The surgical forceps of claim 83 in which said surface coating contains metal particles.

85. Surgical forceps connectable with the bipolar output of an electrosurgical generator having a power output to load impedance characteristic exhibiting a preferred load impedance range for effecting hemostasis of grasped tissue, comprising:

a first tine connectable with said output of first polarity and extending longitudinally to a first tip region having an inwardly disposed electrically conductive first tissue grasping surface with a first periphery of predetermined shape and extending to a tip periphery;

a second tine connectable with said output of second polarity and extending longitudinally to a second tip region having an inwardly disposed electrically conductive second tissue grasping surface with a second periphery of predetermined shape and extending to a tip periphery, said first and second tip regions being mutually oppositely disposed in alignment and relatively movable from an open toward a closed orientation for grasping tissue;

an electrically insulative spacer assembly fixed to at least one said first and second tissue grasping surface and having a configuration for spacing said first and second grasping surfaces apart a distance, T, when said first and second tines are in said closed orientation, said spacer assembly including a first array of parallel strips of insulative material fixed to said first tissue grasping surface at said first tip region, extending transversely to the longitudinal extent of said first tine, one said strip of insulative material being located at said outer periphery of said first tip, said distance, T, being selected to derive a load impedance within said desired load impedance range when said first and second grasping surfaces are grasping tissue while spaced apart substantially about said distance, T, said configuration being effective to derive current paths between said first and second grasping surfaces corresponding with said load competence: and said first and second tissue grasping surfaces being coated with an electro-deposited, biocompatible metallic layer.

86. The surgical forceps of claim 85 in which said electrically insulative spacer assembly spacing distance, T, has minimum value of about 0.003 inch.

87. The surgical forceps of claim 86 in which said spacer assembly includes a second array of parallel strips of insulative material fixed to said second tissue grasping surface.

* * * * *